(12) United States Patent
Warnecke

(10) Patent No.: US 8,597,631 B2
(45) Date of Patent: Dec. 3, 2013

(54) LINEAR SELF-ELIMINATING OLIGOMERS

(75) Inventor: André Warnecke, Freiburg (DE)

(73) Assignee: KTB Tumorforschungsgesellschaft mbH, Freiburg Im Breisgau (DE)

( * ) Notice: Subject to any disclaimer, the term of this patent is extended or adjusted under 35 U.S.C. 154(b) by 222 days.

(21) Appl. No.: 12/994,247

(22) PCT Filed: Apr. 30, 2009

(86) PCT No.: PCT/EP2009/003153
§ 371 (c)(1),
(2), (4) Date: Feb. 10, 2011

(87) PCT Pub. No.: WO2009/141050
PCT Pub. Date: Nov. 26, 2009

(65) Prior Publication Data
US 2012/0270937 A1 Oct. 25, 2012

(30) Foreign Application Priority Data
May 23, 2008 (EP) .................... 08009514

(51) Int. Cl.
*A61K 31/74* (2006.01)
(52) U.S. Cl.
USPC .................................... 424/78.17
(58) Field of Classification Search
None
See application file for complete search history.

(56) References Cited

U.S. PATENT DOCUMENTS
2006/0269480 A1 11/2006 Amir et al.

FOREIGN PATENT DOCUMENTS
WO WO 2004/043493 A 5/2004
WO WO 2008/053479 A 5/2008

OTHER PUBLICATIONS

Amir, R.J. et al., Prodrug activation gated by a molecular or logic trigger, Angewandte Chemie, International Edition, Jul. 11, 2005, vol. 44, Issue 28, pp. 4378-4381.
Amir, R.J. et al., Receiver-amplifier, self-immolative dendritic device, Chem. Eur. J., 2007, vol. 13, pp. 812-821.
International Search Report dated Nov. 12, 2009, for International Application No. PCT/EP2009/003153.
Kratz et al., Prodrug strategies in anticancer chemotherapy, CHEMMEDCHEM, Jan. 11, 2008, vol. 3, Issue 20, pp. 20-53.
Warnecke, A. et al., 2,4-BIS(Hydroxymethyl)Alanine as a building block for oligomers with self-eliminating and multiple release properties, J. Org. Chem., Feb. 15, 2008, vol. 73, pp. 1546-1552.

*Primary Examiner* — Paul Dickinson
(74) *Attorney, Agent, or Firm* — Knobbe, Martens, Olson & Bear, LLP

(57) ABSTRACT

The present invention relates to a linear self-eliminating oligomer comprising one or more cleavable triggers, linker units, effector units and a carrier, and a pharmaceutical composition comprising said oligomer.

15 Claims, 12 Drawing Sheets

Activation

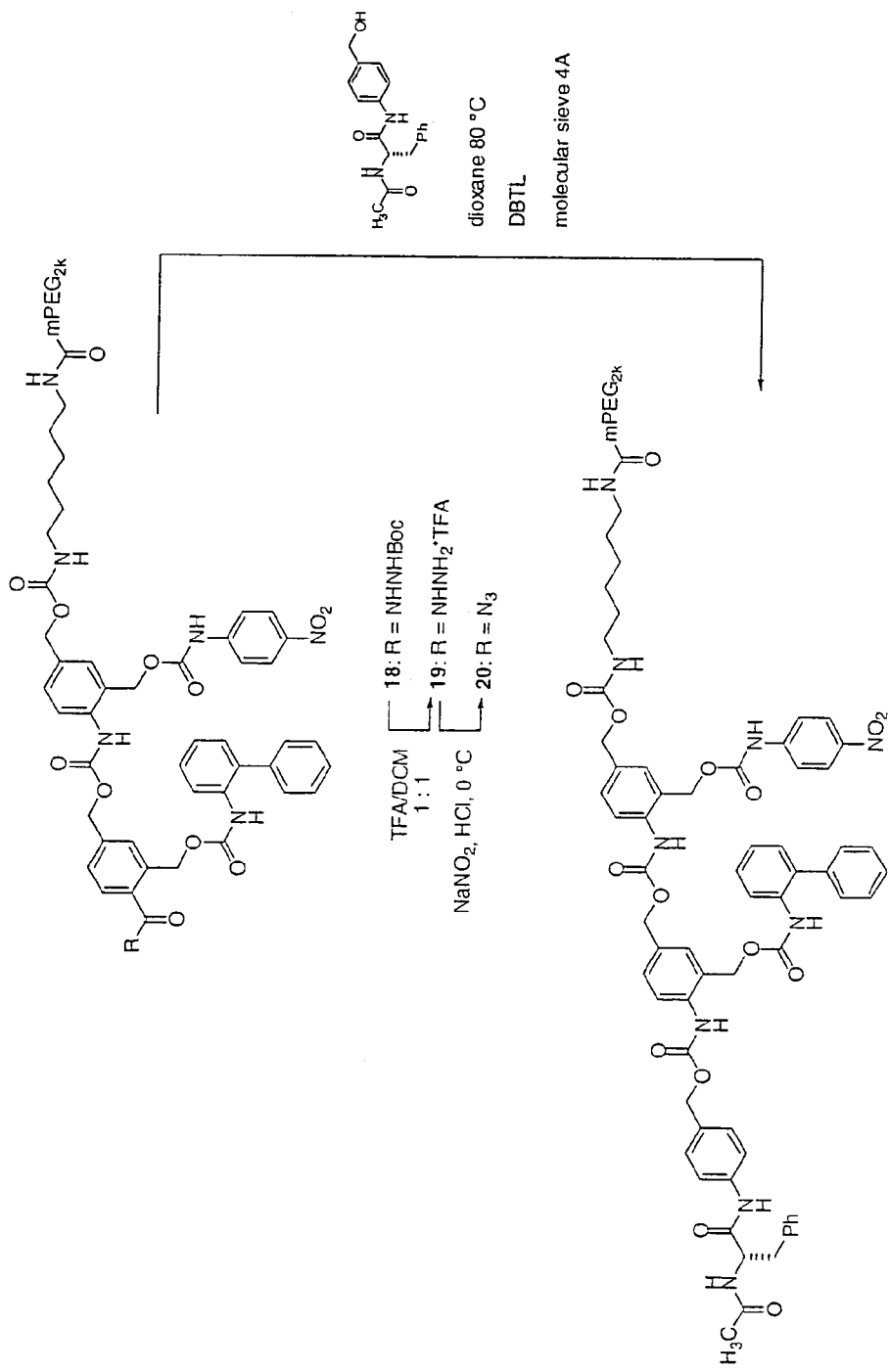
Figure 5c (continuation)

LINEAR SELF-ELIMINATING OLIGOMERS

This application is the U.S. National Phase of International Application No. PCT/EP2009/003153, filed Apr. 30, 2009, designating the U.S. and published in English as WO 2009/141050 on Nov. 26, 2009 which claims the benefit of European Patent Application No. 08009514.4 filed May 23, 2008.

The present invention relates to a linear self-eliminating oligomer comprising one or more cleavable triggers, linker units, effector units and a carrier, and a pharmaceutical composition comprising said oligomer.

Most of the drugs used at present are compounds having low molecular weights and exhibit, when systemically administered to a patient, a high plasma clearance or total body clearance. Furthermore, said low molecular weight compounds show a high tendency to penetrate body tissues by diffusion, resulting in a uniform biodistribution. These are the two main reasons why only small quantities of the drug reach the site of action and, due to distribution over healthy tissues of the body, said drugs give rise to problematic side-effects. These disadvantages are of particular concern for those drugs having a high cytotoxic potential, such as cytotoxic agents, immunosuppressive agents or virostatic agents.

Several strategies have been pursued for improving the selectivity of low molecular weight drugs and thus to increase the concentration of the active agent in the desired tissue, while the concentration of the same is decreased in healthy tissues in order to reduce side-effects.

In this context, the prodrug approach has been developed according to which the drug is administered to an organism in an inactive or less active form and is converted, e.g. by metabolization, into the active form.

For example, antibodies, peptides or synthetic polymers have been investigated as drug carriers for the development of prodrugs (Kratz, F.; Müller, I. A.; Ryppa, C.; Warnecke, A. *Chem Med Chem* 2008, 3, 20-53; R. Duncan, *Nat. Rev. Drug Discovery* 2003, 347-360).

However, although such prodrugs have been shown to allow a more specific delivering of the active agent to the target tissue in most cases, a variety of biochemical mechanisms is known which lead to a decreased efficacy of the respective drug.

In recent years, self-immolative dendrimers have been developed as promising new prodrugs (reviewed in: Shabat, D. *J. Polym. Sci., Polym. Chem.* 2006, 44, 1569-1578; D. V. McGrath, *Mol. Pharm.* 2005, 2, 253-263). Such dendrimers have a complex molecular structure and are designed for a controlled and multiple release of small molecules. Based on self-eliminating linkers as branching units, self immolative dendrimers can be terminally loaded with various effector and/or reporter molecules. Activation at the focal point initiates a cascade of elimination reactions which lead to a breakdown of the whole dendritic scaffold with a concomitant release of the molecular payload. This simultaneous multiple release of effector molecules upon a single activation step makes these compounds attractive for a use as intelligent prodrugs.

However, only a restricted number of drug molecules fit into the limited space of the outer shell of the dendrimer. G3 dendrons with eight small dye molecules and a G2 dendron with four molecules of the bulky drug paclitaxel are the largest self-eliminating dendrimer conjugates which could be synthesized up to now. Furthermore, dendritic structures are not suitable for conveniently combining different drugs. For instance, 13 reaction steps were necessary to synthesize a G1 dendrimer that was loaded with one molecule each of the anticancer drugs camptothecin, etoposide, and doxorubicin (D. Shabat et al., *Angew. Chem. Int. Ed.* 2005, 44, 716-720).

In order to overcome the above drawbacks, linear self-eliminating (LSE) systems have been proposed (A. Warnecke, F. Kratz, *J. Org. Chem.* 2008, 73, 1546-1552). Such linear systems are based on branched self-eliminating linkers as monomer units which may be the same as for self-immolative dendrimers. Chemical or enzymatic activation of a trigger causes the molecule to disassemble in two directions, i.e. the bonds between two linkers that form the linear backbone as well as the bonds between the linkers and the effector molecules are cleaved by elimination reactions. Such systems are schematically illustrated in FIG. 1a, where T represents the trigger, L represents the self-eliminating linkers, and E represents the effectors. By activation of the trigger T, three linker units L and four effector units E are released. FIG. 1b shows the synthesis of a respective model compound, wherein the effector is tryptamine and the trigger is a p-nitrobenzyloxycarbonyl group which can be activated via reduction. In particular, the known approach for the construction of such oligomers makes use of a two-step procedure, namely (1) conversion of the 4-hydroxybenzyl group into an activated 4-nitrophenyl (Np) carbonate, and (2) appending another linker through its amino group by forming a carbamate bond.

However, it is not possible to employ linker-effector derivatives as building blocks in this approach, since effective linkers with an unprotected amino group will immediately undergo elimination of the effector. Thus, it is necessary first to synthesize the oligomer backbone having protected side chains in the linker units, deprotecting the side chains and finally attaching the effector units (FIG. 1b). Thus, LSE systems being loaded with different effector units are only available with significant additional synthetic efforts.

Moreover, the above LSE system being comprised of linker-effector units cannot be used as a prodrug, since it is not bound to a suitable carrier which is necessary from the viewpoint of delivering the active agent to the target tissue.

However, even if a LSE system is bound to a carrier, an arrangement where the trigger is located between the carrier and the linker units is considered to have a detrimental effect on the step of cleaving the trigger for sterical reasons. Moreover, the cleavage of the trigger leads to a complete deattachment of the linker-effector units from the carrier, which leads to solubility problems in aqueous media. However, alternative arrangements of the trigger, the carrier and the linker units are generally very difficult to realize.

Therefore, the technical problem underlying the present invention is to provide a linear self-eliminating oligomer which is suitable to release effector molecules upon activation, which can be loaded with different effector molecules in a straightforward synthetic manner, which is bound to a suitable carrier and which does not lead to a complete deattachment of the linker-effector units from the carrier upon activation of the trigger.

According to the present invention, the above technical problem is solved by providing a linear self-eliminating (LSE) oligomer having the following formula (I):

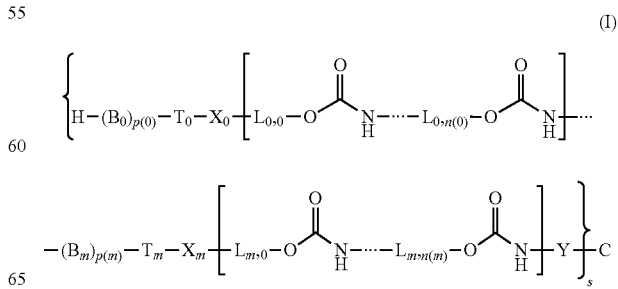

wherein $T_{i\ (i=0\ to\ m)}$ is a trigger group which can be cleaved hydrolytically, enzymatically, pH-dependently, thermally, photochemically, oxidatively or reductively;

$X_{i\ (i=0\ to\ m)}$ is NH, O or S;

C is a carrier selected from the group consisting of serum proteins, antibodies or antibody fragments, synthetic polymers, dendrimers, peptides, growth factors, receptor-binding ligands, polysaccharides, microparticles and nanoparticles;

Y is a single bond or a spacer group;

m is 0 to 5;

s is 1 to 100;

$n(i)_{(i=0\ to\ m)}$ is independently 1 to 30;
with the proviso that n(0) is at least 2 when m=0;

$p(i)_{i=0\ to\ m}$ is independently 0 or 1;
with the proviso that p(0) is 0;

$L_{i,k\ (i=0\ to\ m\ and\ k=0\ to\ n(i))}$ is a linker unit independently selected from one of the following structures (II), (III), (IV) or (V):

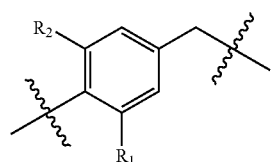
(II)

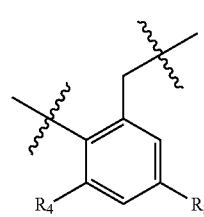
(III)

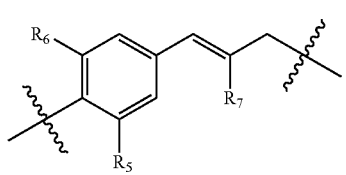
(IV)

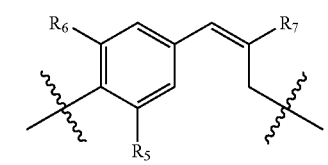
(V)

$B_{i\ (i=0\ to\ m)}$ is a blocking unit having the following structure:

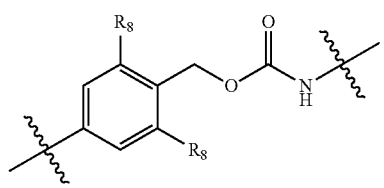

$R_1$ is selected from H or one of the following residues:

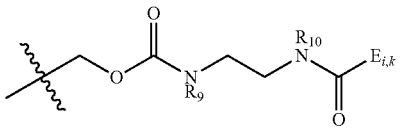

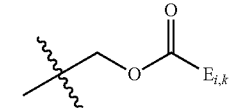

$R_2$ is selected from H, methyl, $CH_3O$, halogen, acetyl, alkoxycarbonyl, $NO_2$ or one of the following residues:

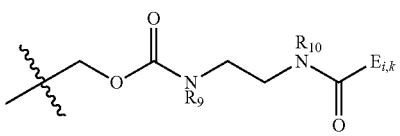

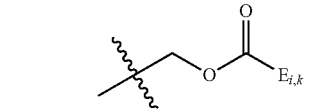

$R_3$ is selected from H or one of the following residues:

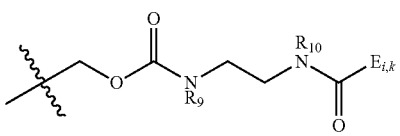

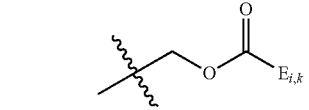

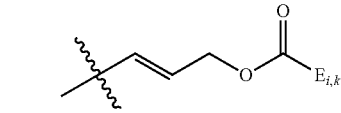

$R_4$ is selected from H, methyl, $CH_3O$, halogen, acetyl, alkoxycarbonyl, $NO_2$ or one of the following residues:

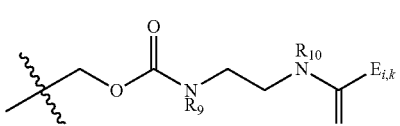

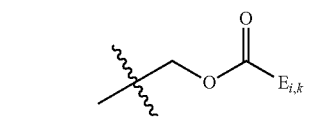

$R_5$ is selected from H or one of the following residues:

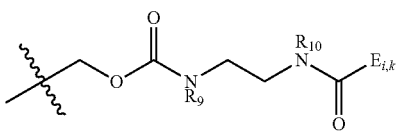

-continued

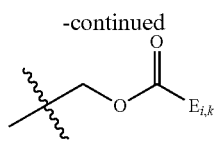

$R_6$ is selected from H, methyl, $CH_3O$, halogen, acetyl, alkoxycarbonyl, $NO_2$ or one of the following residues:

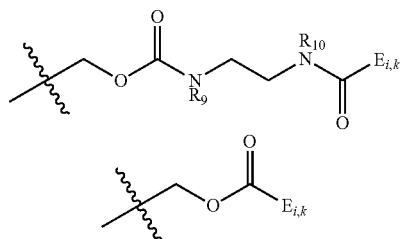

$R_7$ is selected from H or one of the following residues:

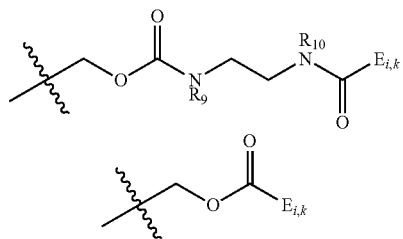

$R_8$ is independently selected from a linear or branched $C_{1-8}$ alkyl group, a phenyl group, a naphthyl group, a biphenyl group or a vinyl benzene group;
$R_9$ is independently selected from hydrogen or a linear or branched $C_{1-8}$ alkyl group;
$R_{10}$ is independently selected from hydrogen or a linear or branched $C_{1-8}$ alkyl group;
$E_{i,k}$ $(i=0\ to\ m\ and\ k=0\ to\ n(i))$ is an effector group independently containing a dye, a diagnostic agent or a pharmaceutically active compound, wherein the dye, diagnostic agent or pharmaceutically active compound is bound to the linker unit $L_{i,k}$ via an amino, hydroxy or mercapto group;
with the proviso that the linear self-eliminating oligomer contains in total at least two effector units.

According to the present invention, the term "self-eliminating oligomer" refers to oligomers of linker-effector units that disassemble upon activation of at least one trigger unit. Said activation can be achieved by physical, chemical or enzymatic means. Preferably, activation of the trigger causes the molecule to disassemble in two directions, i.e. the bonds between two linkers that form the linear backbone of the oligomer as well as the bonds between the linkers and the effector molecules are cleaved by elimination reactions.

The linear self-eliminating oligomer according to the present invention comprises m+1 trigger units, wherein m is 0 to 5; i.e. the oligomer of the present application contains 1 to 6 trigger units. Each trigger unit is separately denoted by $T_i$, wherein the index i reflects a number from 0 to m. Accordingly, each trigger unit can be identified individually in the general formula (I) by its index i. The number of trigger units in the LSE oligomer of the present invention corresponds to the number of blocks i (i=0 to m) which build up the LSE oligomer.

The linear self-eliminating oligomer according to the present invention can be exemplarily illustrated by the schemes shown in FIGS. 2a and 2b. In particular, in case m is 0, the linear self-eliminating oligomer can be represented by the scheme of FIG. 2a. In this example, the LSE oligomer only contains one block (i=0) with a trigger unit $T_0$, three linker-effector units $L_{0,0}$-$E_{0,0}$, $L_{0,1}$-$E_{0,1}$ and $L_{0,2}$-$E_{0,2}$ (i.e. n(0)=2), and the carrier C. The linear self-eliminating oligomer of FIG. 2b contains one terminal block as well as two further blocks (i.e. m=2). In the oligomers of FIGS. 2a and 2b it is possible that the effector units are different or the same. In the case of m=0, the linear self-eliminating oligomer of the present invention disassembles upon a single triggering event (i.e. cleavage of the only trigger unit T) under complete degradation of the linear backbone, accompanied by the release of the side-chain bound effector units E (cf. FIG. 2c).

In a preferred embodiment of the present invention, m is 0. This represents the simplest structure of the claimed LSE oligomer containing only one block. Such an oligomer can be completely disassembled by a single triggering event. In another preferred embodiment, m is 1 to 5, more preferably 2 to 5, and even more preferably 3 to 5. In this case, the LSE oligomer contains more than one block, namely m+1 blocks and m+1 trigger units. Said m+1 trigger units may be different and thus, the LSE oligomer can be adapted to disassemble stepwise upon separate activation of the different trigger units.

An example for an arrangement with more than one trigger unit is shown in FIG. 2b and this arrangement can serve as a release system with a pre-defined (programmed) and complex release behavior. Similar to a computer program, the) release of effector molecules (output) is controlled by different signals (input). The signal processing of an LSE oligomer can be readily translated into a flowchart according to ISO 5807 as exemplarily shown in FIG. 2d (flowchart notation of the LSE oligomer depicted in FIG. 2b). For the oligomer of FIG. 2b, activation of the first trigger unit $T_0$ initiates the release of the effector units $E_{0,0}$, $E_{0,1}$ and $E_{0,2}$ and exposes trigger unit $T_1$. Specific activation of trigger unit $T_1$ further results in the release of effector unit $E_{1,0}$ and the exposure of trigger unit $T_2$. Specific activation of trigger unit $T_2$ eventually results in the release of effector unit $E_{2,0}$. For being an equivalent implementation of the flowchart depicted in FIG. 2d, the chemical realization of the LSE oligomer in FIG. 2b has to ensure that the internal trigger groups $T_i(i>0)$ are stable against activation unless they become exposed, i.e. by activation of $T_{i-1}$. Thus, a chemical realization of stable internal trigger units may include the use of blocking units $B_i$.

Using drugs as effector units paves the way for innovative therapeutic strategies against various diseases. Thus, the LSE oligomers of the present invention can provide both a site-specific and a controlled release of drugs.

The facility of liberating different drugs in defined ratios upon a single triggering event makes LSE oligomers an ideal platform for the development of novel combination therapeutics. For instance, FIG. 2a shows an example for a LSE oligomer which is capable of releasing three different drugs in a ratio of 1:1:1 after activation of $T_0$. As the drugs are released at their site of action, e.g. intracellularly in tumor tissue, problems resulting from different pharmacokinetics as experienced in conventional combination treatment can be circumvented (Mayer, L. D.; Janoff, A. S. *Molecular Interventions* 2007, 7, 216-223). In contrast to previous approaches using dendritic structures (Haba, K.; Popkov, M.; Shamis, M.; Lerner, R. A.; Barbas, C. F., 3rd; Shabat, D. *Angew. Chem. Int. Ed.* 2005, 44, 716-720), employing LSE oligomers is a more versatile strategy that facilitates the variation of drug ratios.

In addition, even more complex therapeutic strategies can be pursued by fully exploiting the program-like nature of LSE oligomers. For instance, FIG. 2b shows an) example for a LSE oligomer which is capable of specifically reacting to cellular responses which may occur after the release of the drugs $E_{0,0}$, $E_{0,1}$ and $E_{0,2}$ (e.g. as a consequence of the development of drug resistance). Said cellular responses may be indicated by the upregulation of a certain enzyme which in turn can be utilized for the activation of the trigger unit $T_1$ and the subsequent release of the additional drug $E_{1,1}$.

According to the present invention, the trigger units $T_i$ are units which can be cleaved hydrolytically, enzymatically, pH-dependently, thermally, photochemically, oxidatively or reductively, i.e. by physical or chemical means.

According to a preferred embodiment of the present invention, the trigger unit comprises one or more hydrolytically cleavable bonds, the hydrolysis of which initiates the disassembling of the linear backbone of the linear self-eliminating oligomer. Examples for hydrolytically cleavable bonds are ester bonds.

In another preferred embodiment of the present invention, the trigger unit may be cleavable by an enzyme. For example, the trigger unit of the present invention may contain at least one peptide bond which is preferably located within a cleavable peptide sequence of a protease. A peptide bond can therefore be implemented by the insertion of a respective peptide sequence into the cleavable trigger unit. Suitable enzymes are, for example, proteases and peptidases, e.g. matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. Preferred examples of proteases according to the present invention are in particular MMP-2, MMP-3 and MMP-9, cathepsin B, H, L and D, plasmin, urokinase, and prostate-specific antigen (PSA). It is particularly preferred that the internal trigger units $T_i(i>0)$ may be activated enzymatically.

Preferred peptide sequences that are incorporated in the trigger unit $T_i$ of the LSE oligomer of the present invention are -Arg-, -Arg-Arg-, -Phe-Arg-, -Phe-Cit-, -Ile-Pro-Lys-, -Lys-Lys-, -Arg-Lys-, -Ala-Leu-Ala-Leu-, -Phe-Lys-, -Phe-Lys-Ala-, -Val-Cit-, -Val-Arg-, -Ala-Phe-Lys-, -D-Ala-Phe-Lys-, -Ser-Ser-Tyr-Tyr-Ser-Arg-, -Phe-Pro-Lys-Phe-Phe-Ser-Arg-Gln-, -Lys-Pro-Ile-Glu-Phe-Nph-Arg-Leu-, -Gly-Pro-Leu-Gly-Ile-Ala-Gly-Gln-, -Gly-Pro-Leu-Gly-Ile-Ala-Gly-Gln-, -Gly-Pro-Gln-Gly-Ile-Trp-Gly-Gln-, -Gly-Phe-Leu-Gly-.

In another preferred embodiment of the present invention, the trigger unit may be cleavable by non-proteolytic enzymes such as β-glucuronidase, penicillin amidases, phosphatases and phosphoramidases.

In another preferred embodiment of the present invention, the trigger unit may be cleavable by catalytic antibodies.

In another preferred embodiment of the present invention, the trigger unit according to the present invention contains at least one acid-labile bond. Examples of acid-labile bonds are ester, acetal, ketal, imine, hydrazone, acylhydrazone and sulfonylhydrazone bonds and bonds containing a trityl group.

In another preferred embodiment of the present invention, the trigger unit contains a reductively cleavable group and may have one of the following structures:

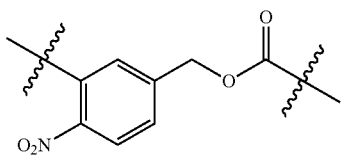

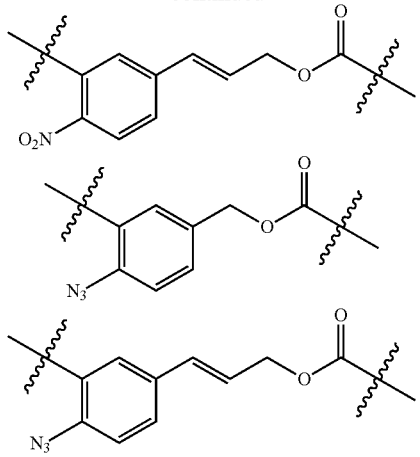

In the case that the above reductively cleavable group contains a nitro group, 1,6- or 1,8-elimination is initiated upon reduction of the nitro group to an amino or hydroxyl amino group, leading to the disassembling of the linear backbone of the oligomer of the present invention. Reduction can be performed e.g. by using zinc under acidic conditions.

When using the LSE oligomers of the present invention for therapeutic strategies) against various diseases, it is especially preferred that the terminal trigger unit $T_0$ may be activated by disease-related signals, e.g. upregulated proteolytic enzymes or a change in pH, or activated externally, e.g. by radiation.

The trigger unit $T_i$ is connected to the linker groups $L_i$ via the group $X_i$, which is independently selected from O, S and NH. As for the trigger unit $T_i$, the linear self-eliminating oligomer according to the present invention comprises m+1 groups $X_i$, wherein m is 0 to 5. Each of these units is separately denoted by $X_i$, wherein the index i reflects a number from 0 to m. Accordingly, each unit X can be identified separately in the general formula (I) by its index i.

In the case of more than one trigger units, i.e. in the case when m is 1 to 5, it is desirable that the internal trigger groups $T_i$ (i>0) are prevented from an activation unless the preceding block has completely disassembled. According to the present invention, this may be achieved by providing an optional blocking unit $B_i$ directly preceding the trigger unit $T_i$. Said blocking unit has the following structure:

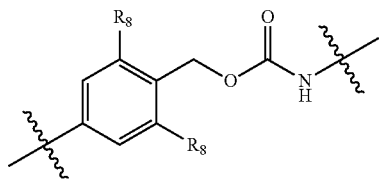

wherein $R_8$ is independently selected from a linear or branched $C_{1-8}$ alkyl group, a phenyl group, a naphthyl group, a biphenyl group or a vinyl benzene group. Said blocking group preferably comprises bulky side chains which provide a sterical hindrance at the trigger unit leading to a decelerated cleavage of said trigger unit. Preferably, $R_8$ is a tert-butyl group. In particular, by providing a blocking unit $B_i$ close to a trigger unit, said trigger unit is accessible e.g. for an enzyme only after complete disassembling of the linker units of the previous block i-1 including said blocking unit $B_i$ in the self-eliminating oligomer.

Each block i (i=0 to m) may contain one blocking unit $B_i$ which is represented in general formula (I) by index p(i) which may be 0 or 1 independently for each block i. Accordingly, in case p(i) is 0, the respective block i does not contain a blocking unit, whereas in the case p(i) is 1, the respective block i contains a blocking unit. In the first block (i.e. for i=0), no blocking unit should be present. Accordingly, p(0) is 0.

The carrier C of the LSE oligomer of the present invention is selected from the group consisting of serum proteins, antibodies or antibody fragments, synthetic polymers, dendrimers, peptides, growth factors, receptor-binding ligands, polysaccharides, microparticles and nanoparticles. The carrier in general contains suitable functional groups such as hydroxy, amino or thiol groups to bind to the terminal linker $L_{m,n(m)}$ of the linear self-eliminating oligomer. If necessary, these groups can be introduced in the carrier molecule by chemical modification through techniques known to those skilled in the art (Kratz et al., (2001): Anticancer drug conjugates with macromolecular carriers, in Polymeric Biomaterials, second edition, S. Dumitriu, Marcel Dekker, New York, Chapter 32, 851-894). Suitable serum proteins are for example human serum transferrin and serum albumin. Suitable synthetic polymers are poly(ethylene glycols) (PEGs) having a mass e.g. ranging from 5,000 to 200,000 Da. In a preferred embodiment of the present invention, the carrier C is a synthetic polymer selected from the group consisting of poly(ethylene glycol) (PEG), monomethoxy PEG (mPEG), polyglycerol (PG), poly(ethylene imine) (PEI) and N-(2-hydroxypropyl)methacrylamide (HPMA) copolymers.

The carrier may be a polyfunctional carrier. Thus, the carrier may contain one or more oligomer chains which is represented in general formula (I) by the index s. In particular, in the LSE oligomer of the present invention, s oligomer chains may be bound to the carrier C, wherein s is 1 to 100. In a preferred embodiment of the present invention, s is 1 to 10, in a more preferred embodiment of the present invention, s is 1 or 2.

When using the LSE oligomers of the present invention for therapeutic strategies against various diseases, it is especially preferred that the carrier molecule C is selected from targeting moieties such as antibodies or receptor-binding ligands or from macromolecules with inherent targeting properties, e.g. for passively targeting solid tumors (Kratz, F.; Müller, I. A.; Ryppa, C.; Warnecke, A. *Chem Med Chem* 2008, 3, 20-53).

The carrier C is connected to the terminal linker $L_{m,n(m)}$ of the LSE oligomer via the group Y which may be a single bond or a spacer group. A suitable spacer group is for example a group having the following structure:

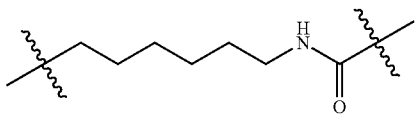 [SMILES: *CCCCCCNC(*)=O]

The carrier C is located at one end of the LSE oligomer, whereas the trigger unit $T_0$ is located at the other end of the LSE oligomer according to the present invention. Thus, upon activation of the first trigger, the oligomer chain of the linker-effector units is not completely deattached from the carrier as it would be the case if the carrier was located at the first trigger unit. According to the present invention, the linker-effector units keep attached to the carrier until the degradation of the LSE oligomer backbone is completed which is advantageous from the viewpoint of solubility of the oligomer in aqueous media.

Moreover, the LSE oligomer of the present invention contains linker units $L_{i,k}$. In particular, each block i may independently contain n linker units which is denoted by the index n(i). The index n(i) independently represents an integral number from 1 to 30, with the proviso that n(0) is at least 2, when m is 0. Each linker unit is separately denoted by $L_{i,k}$, wherein the index i refers to the respective block in which the linker group is contained, and reflects a number from 0 to m, and the index k refers to the specific linker group within each block i and reflects a number from 0 to n(1). Accordingly, each linker group can be identified individually in the general formula (I) by its indices i and k. In a preferred embodiment of the present invention, n(i) is independently a number from 1 to 10, more preferably a number from 2 to 5. The linker units $L_{i,k}$ basically represent the linear backbone of the linear self eliminating oligomer which disassemble upon activation of the trigger units $T_i$. In case, m is 0, the LSE oligomer only contains linker units $L_{0,k}$.

According to the present invention, the linker units $L_{i,k}$ are independently selected from one of the following structures (II), (III), (IV) or (V):

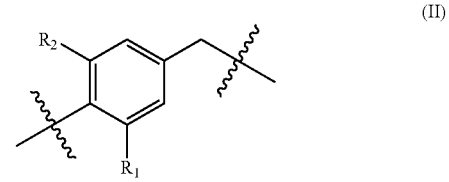

(II)

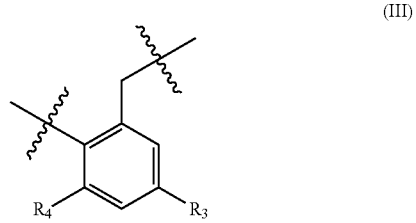

(III)

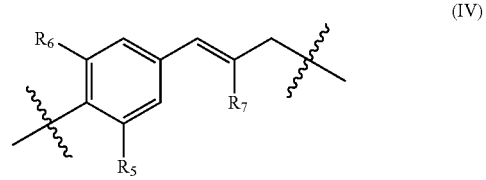

(IV)

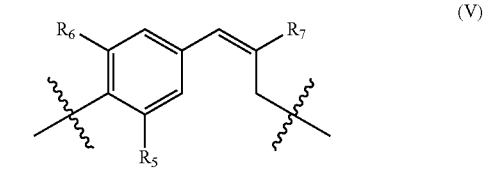

(V)

Upon activation of the trigger unit $T_i$, the above structures disassemble via a 1,6-benzylic elimination, a 1,4-benzylic elimination and a 1,8-elimination, respectively. The respective elimination mechanisms are shown in FIG. 3, wherein X represents the free group $X_i$ of general formula (I) after activation of the trigger unit.

In the linker unit having the structure (II), $R_1$ is either H or one of the following residues (XI) or (XII) bearing an effector unit $E_{i,k}$:

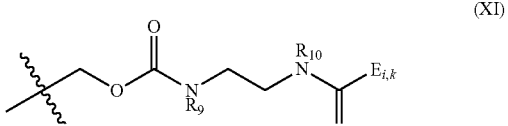

(XI)

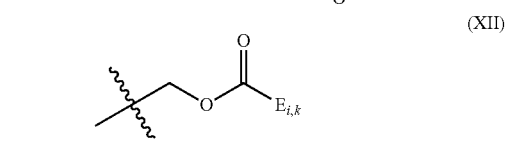

(XII)

wherein the effector group $E_{i,k}$ is bound to the linker unit via an amino, hydroxy or mercapto group. When $R_1$ corresponds to the above residue (XII), then $E_{i,k}$ is preferably bound to the linker unit via an amino group since the resulting carbamate bond is sufficiently stable against hydrolysis under physiological conditions tolerating a wide range of pH. When $R_1$ corresponds to the above residue (XI), then $E_{i,k}$ is preferably bound to the linker unit via a hydroxy group. With the incorporation of an ethylene diamine-based cyclization linker, only stable carbamate bonds are generated. The effector is then released by a two-step reaction comprising benzyl elimination and subsequent cyclization of the ethylene diamine moiety.

$R_9$ and $R_{10}$ are independently from each other selected from hydrogen or a linear or branched $C_{1-8}$ alkyl group and are preferably a methyl group.

$R_2$ is selected from H, methyl, $CH_3O$, halogen, acetyl, alkoxycarbonyl, $NO_2$ or one of the following residues (XI) or (XII) bearing an effector unit $E_{i,k}$:

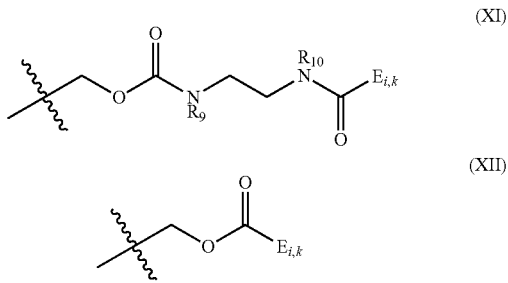

wherein the effector group $E_{i,k}$ is bound to the linker unit via an amino, hydroxy or mercapto group. When $R_2$ corresponds to the above residue (XII), then $E_{i,k}$ is preferably bound to the linker unit via an amino group since the resulting carbamate bond is sufficiently stable against hydrolysis under physiological conditions tolerating a wide range of pH. When $R_2$ corresponds to the above residue (XI), then $E_{i,k}$ is preferably bound to the linker unit via a hydroxy group. With the incorporation of an ethylene diamine-based cyclization linker, only stable carbamate bonds are generated. The effector is then released by a two-step reaction comprising benzyl elimination and subsequent cyclization of the ethylene diamine moiety.

$R_9$ and $R_{10}$ are independently from each other selected from hydrogen or a linear or branched $C_{1-8}$ alkyl group and are preferably a methyl group.

In a preferred embodiment of the present invention, at least all linker units $L_{i,k}$ with k>0 have above structure (II). It is also preferred that $R_1$ is represented by above residue (XII).

It is further preferred that $R_2$ is hydrogen which is advantageous from the synthetic viewpoint. In another preferred embodiment, $R_2$ is selected from methyl, $CH_3O$, halogen, acetyl, alkoxycarbonyl or $NO_2$. Suitable halogens may be fluorine, chlorine, bromine and iodine. Introducing electron-withdrawing or electron-releasing groups to the aromatic ring is suitable for adjusting (accelerating or retarding) the kinetics of the elimination reactions (Perry, R.; Amir, R. J.; Shabat, D. *New J. Chem.* 2007, 31, 1307-1312). For example, if the desired release behavior of the LSE oligomer of FIG. 2a is a rapid release of effector units $E_{0,0}$ and $E_{0,1}$ followed by a retarded release of $E_{0,2}$, the linker $L_{0,2}$ must be manipulated by the introduction of an appropriate (i.e. electron-releasing) group.

In another preferred embodiment of the present invention, $R_2$ is the same as $R_1$ and represents one of the above residues (XI) or (XII) bearing an effector unit $E_{i,k}$. In this case, it is possible to provide a linker unit $L_{i,k}$ which is loaded with two effector units $E_{i,k}$; i.e. a double loading is provided. According to the present invention, it is especially preferred that both $R_1$ and $R_2$ are represented by residue (XII).

Since the effector units may have a high steric demand, it is possible that the ability of the trigger unit $T_i$ to be cleaved is deteriorated due to neighboring effector units.

Therefore, it is preferable that $R_1$ and $R_2$ are hydrogen in the linker unit $L_{i,0}$ being adjacent to the structural unit $T_i$-$X_i$. By introduction of such a spacer group which does not bear an effector unit $E_{i,0}$, it is possible to minimize the negative influence of bulky effector units $E_{i,k}$ on the cleavage of the trigger unit $T_i$. Such an arrangement is schematically shown in FIG. 2b, where the linker unit $L_{1,0}$ adjacent to the trigger unit $T_1$ does not bear an effector, thus being a mere spacer group.

In the linker unit having the structure (III), $R_3$ is either H or one of the following residues (XI) to (XIII) bearing an effector unit $E_{i,k}$:

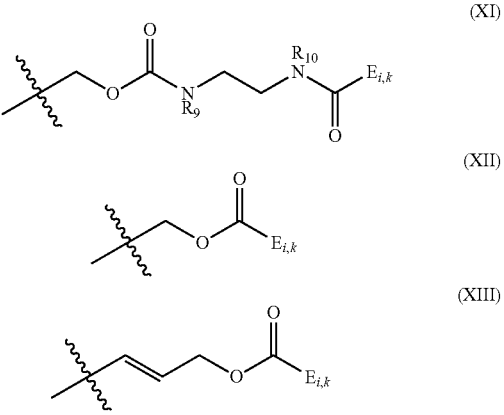

wherein the effector group $E_{i,k}$ is bound to the linker unit via an amino, hydroxy or mercapto group. When $R_3$ corresponds to the above residue (XII) or (XIII), then $E_{i,k}$ is preferably bound to the linker unit via an amino group since the resulting carbamate bond is sufficiently stable against hydrolysis under physiological conditions tolerating a wide range of pH. When $R_3$ corresponds to the above residue (XI), then $E_{i,k}$ is preferably bound to the linker unit via a hydroxy group. With the incorporation of an ethylene diamine-based cyclization linker, only stable carbamate bonds are generated. The effector is then released by a two-step reaction comprising benzyl elimination and subsequent cyclization of the ethylene diamine moiety.

$R_9$ and $R_{10}$ are independently from each other selected from hydrogen or a linear or branched $C_{1-8}$ alkyl group and are preferably a methyl group.

$R_4$ is selected from H, methyl, $CH_3O$, halogen, acetyl, alkoxycarbonyl, $NO_2$ or one of the following residues (XI) or (XII) bearing an effector unit $E_{i,k}$:

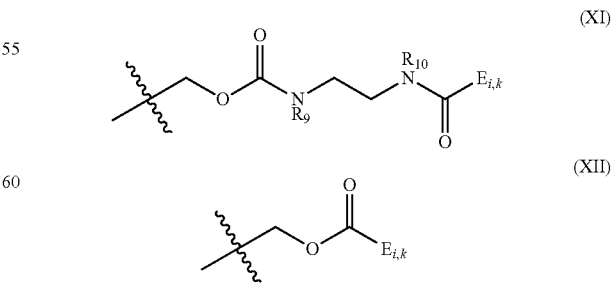

wherein the effector group $E_{i,k}$ is bound to the linker unit via an amino, hydroxy or mercapto group. When $R_4$ corresponds to the above residue (XII), then $E_{i,k}$ is preferably bound to the linker unit via an amino group since the resulting carbamate bond is sufficiently stable against hydrolysis under physiological conditions tolerating a wide range of pH. When $R_4$ corresponds to the above residue (XI), then $E_{i,k}$ is preferably bound to the linker unit via a hydroxy group. With the incorporation of an ethylene diamine-based cyclization linker, only stable carbamate bonds are generated. The effector is then released by a two-step reaction comprising benzyl elimination and subsequent cyclization of the ethylene diamine moiety.

$R_9$ and $R_{10}$ are independently from each other selected from hydrogen or a linear or branched $C_{1-8}$ alkyl group and are preferably a methyl group.

In a preferred embodiment of the present invention, at least all linker units $L_{i,k}$ with k>0 have above structure (III). It is also preferred that $R_3$ is represented by residue (XII).

It is further preferred that $R_4$ is hydrogen which is advantageous from the synthetic viewpoint. In another preferred embodiment, $R_4$ is selected from methyl, $CH_3O$, halogen, acetyl, alkoxycarbonyl or $NO_2$. Suitable halogens may be fluorine, chlorine, bromine and iodine. Introducing electron-withdrawing or electron-releasing groups to the aromatic ring is suitable for adjusting (accelerating or retarding) the kinetics of the elimination reactions (Perry, R.; Amir, R. J.; Shabat, D. *New J. Chem.* 2007, 31, 1307-1312). For example, if the desired release behavior of the LSE oligomer of FIG. 2a is a rapid release of effector units $E_{0,0}$ and $E_{0,1}$ followed by a retarded release of $E_{0,2}$, the linker $L_{0,2}$ must be manipulated by the introduction of an appropriate (i.e. electron-releasing) group.

In the linker units having above structure (IV) and (V), $R_5$ is either H or one of the following residues (XI) or (XII) bearing an effector unit $E_{i,k}$:

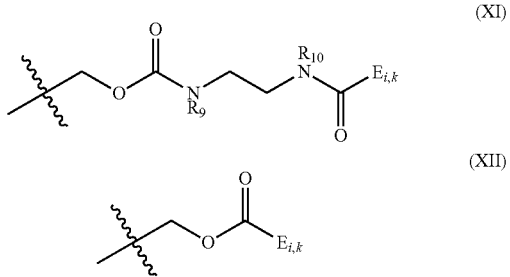

(XI)

(XII)

wherein the effector group $E_{i,k}$ is bound to the linker unit via an amino, hydroxy or mercapto group. When $R_5$ corresponds to the above residue (XII), then $E_{i,k}$ is preferably bound to the linker unit via an amino group since the resulting carbamate bond is sufficiently stable against hydrolysis under physiological conditions tolerating a wide range of pH. When $R_5$ corresponds to the above residue (XI), then $E_{i,k}$ is preferably bound to the linker unit via a hydroxy group. With the incorporation of an ethylene diamine-based cyclization linker, only stable carbamate bonds are generated. The effector is then released by a two-step reaction comprising benzyl elimination and subsequent cyclization of the ethylene diamine moiety.

$R_9$ and $R_{10}$ are independently from each other selected from hydrogen or a linear or branched $C_{1-8}$ alkyl group and are preferably a methyl group.

$R_6$ is selected from H, methyl, $CH_3O$, halogen, acetyl, alkoxycarbonyl, $NO_2$ or one of the following residues (XI) or (XII) bearing an effector unit $E_{i,k}$:

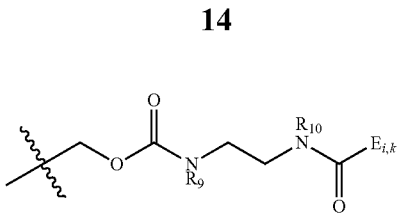

(XI)

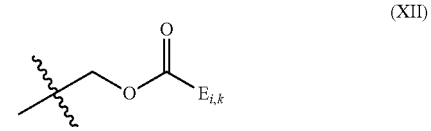

(XII)

wherein the effector group $E_{i,k}$ is bound to the linker unit via an amino, hydroxy or mercapto group. When $R_6$ corresponds to the above residue (XII), then $E_{i,k}$ is preferably bound to the linker unit via an amino group since the resulting carbamate bond is sufficiently stable against hydrolysis under physiological conditions tolerating a wide range of pH. When $R_6$ corresponds to the above residue (XI), then $E_{i,k}$ is preferably bound to the linker unit via a hydroxy group. With the incorporation of an ethylene diamine-based cyclization linker, only stable carbamate bonds are generated. The effector is then released by a two-step reaction comprising benzyl elimination and subsequent cyclization of the ethylene diamine moiety.

$R_9$ and $R_{10}$ are independently from each other selected from hydrogen or a linear or branched $C_{1-8}$ alkyl group and are preferably a methyl group.

$R_7$ is selected from H or one of the following residues (XI) or (XII) bearing an effector unit $E_{i,k}$:

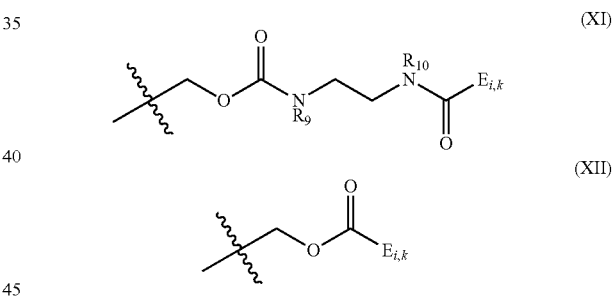

(XI)

(XII)

wherein the effector group $E_{i,k}$ is bound to the linker unit via an amino, hydroxy or mercapto group. When $R_7$ corresponds to the above residue (XII), then $E_{i,k}$ is preferably bound to the linker unit via an amino group since the resulting carbamate bond is sufficiently stable against hydrolysis under physiological conditions tolerating a wide range of pH. When $R_7$ corresponds to the above residue (XI), then $E_{i,k}$ is preferably bound to the linker unit via a hydroxy group. With the incorporation of an ethylene diamine-based cyclization linker, only stable carbamate bonds are generated. The effector is then released by a two-step reaction comprising benzyl elimination and subsequent cyclization of the ethylene diamine moiety.

$R_9$ and $R_{10}$ are independently from each other selected from hydrogen or a linear or branched $C_{1-5}$ alkyl group and are preferably a methyl group.

In a preferred embodiment of the present invention, at least all linker units $L_{i,k}$ with k>0 have above structures (IV) and/or (V). Using above structures (IV) or (V) as a linker unit, it is possible to attach effector units $E_{i,k}$ via all three residues $R_5$, $R_6$ and $R_7$.

However, in a preferred embodiment of the present invention, effector units $E_{i,k}$ are only contained in the groups $R_5$ and $R_7$, even more preferred only in group $R_7$. In case $R_7$ is selected from one of the above effector unit-containing residues, it is preferable that both $R_5$ and $R_6$ are hydrogen. In another preferred embodiment of the present invention, $R_6$ and $R_7$ are hydrogen and $R_5$ is selected from the following residues (XI) or (XII):

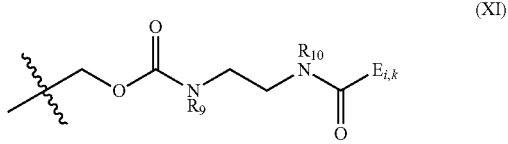

(XI)

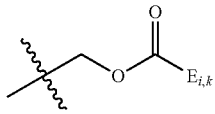

(XII)

In another preferred embodiment, $R_6$ is selected from methyl, $CH_3O$, halogen, acetyl, alkoxycarbonyl or $NO_2$. Suitable halogens may be fluorine, chlorine, bromine and iodine. Introducing electron-withdrawing or electron-releasing groups to the aromatic ring is suitable for adjusting (accelerating or retarding) the kinetics of the elimination reactions (Perry, R.; Amir, R. J.; Shabat, D. *New J. Chem.* 2007, 31, 1307-1312). For example, if the desired release behavior of the LSE oligomer of FIG. 2a is a rapid release of effector units $E_{0,0}$ and $E_{0,1}$ followed by a retarded release of $E_{0,2}$, the linker $L_{0,2}$ must be manipulated by the introduction of an appropriate (i.e. electron-releasing) group.

In another preferred embodiment of the present invention, $R_6$ is the same as $R_5$ and/or $R_7$ and represents one of the above residues bearing an effector unit $E_{i,k}$. In this case, it is possible to provide a linker unit $L_{i,k}$ which is loaded with two or even three effector units $E_{i,k}$; i.e. a multiple loading is provided.

Since the effector units may have a high steric demand, it is possible that the ability of the trigger unit $T_i$ to be cleaved is deteriorated due to neighboring effector units. Therefore, it is preferable that $R_5$, $R_6$ and $R_7$ are hydrogen in the linker unit $L_{i,0}$ being adjacent to the structural unit $T_i$-$X_i$. By introduction of such a spacer group which does not bear an effector unit $E_{i,0}$, it is possible to minimize the negative influence of bulky effector units $E_{i,k}$ on the cleavage of the trigger unit $T_i$.

It is especially preferred that the LSE oligomer of the present invention has one of the following structures, wherein m is 0:

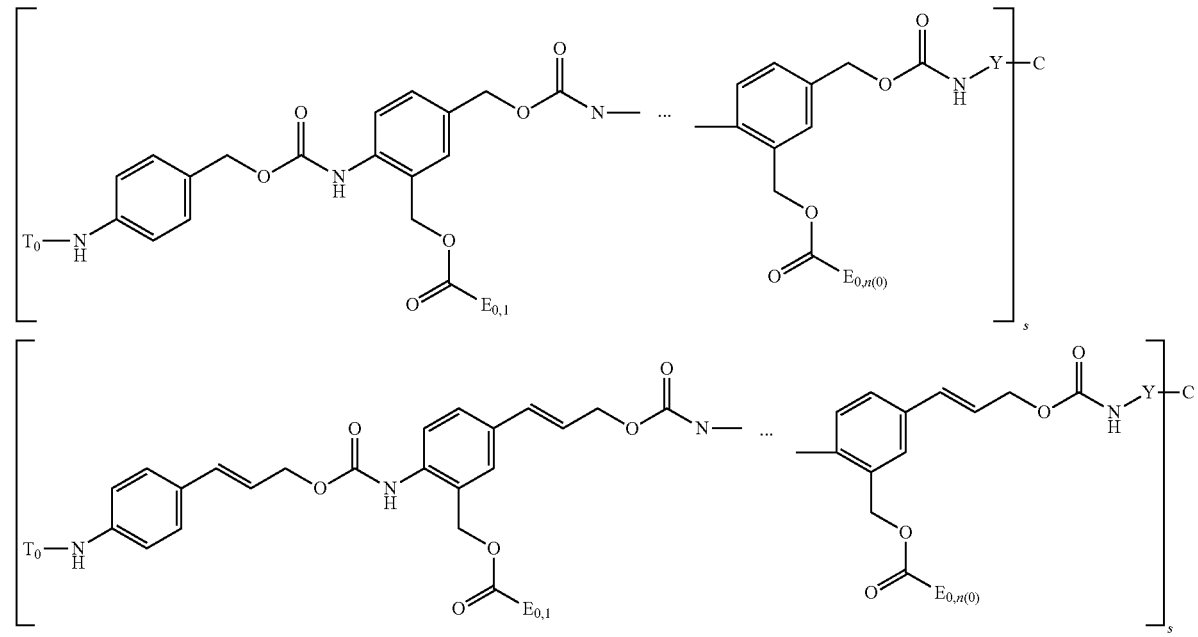

The LSE oligomer according to the present invention contains in total at least two effector units $E_{i,k}$ which are released upon disassembling of the linker units. Said effector units $E_{i,k}$ independently contain a dye, a diagnostic agent or a pharmaceutically active compound, wherein the dye, diagnostic agent or pharmaceutically active compound is bound to the linker unit $L_{i,k}$ via an amino, hydroxy or mercapto group. Preferably, $E_{i,k}$ is bound to the linker unit via an amino group.

According to the present invention, the effector unit $E_{i,k}$ is preferably selected from the group consisting of a cytostatic agent, a cytokine, an immunosuppressant, an antirheumatic, an antiphlogistic, an antibiotic, an analgetic, a virostatic, an antimycotic agent, a transcription factor inhibitor, a cell cycle modulator, a MDR modulator, a vascular disrupting agent, a proteasome or protease inhibitor, an apoptosis modulator, an enzyme inhibitor, an angiogenesis inhibitor, a hormone or hormone derivative, a radioactive substance, a light emitting substance, or a light absorbing substance. Preferably, the effector unit $E_{i,k}$ is a cytostatic agent selected from the group consisting of N-nitrosoureas, the anthracyclines doxorubicin, daunorubicin, epirubicin, idarubicin, mitoxantrone and ametantrone, and any derivatives thereof; the alkylating agents chlorambucil, bendamustine, melphalan, and oxazaphosphorines, and any derivatives thereof; the antimetabolites 5-fluorouracil, 2'-deoxy-5-fluorouridine, cytarabine, cladribine, fludarabine, pentostatine, gemcitabine, 6-thioguanine, 6-mercaptopurine and any derivatives thereof; the folic acid antagonists methotrexate, raltitrexed, pemetrexed and plevitrexed, the taxanes paclitaxel and docetaxel, and any derivatives thereof; the camptothecins topotecan, irinotecan (CPT-11), SN-38, 10-hydroxycamptothecin, GG211, lurtotecan, 9-aminocamptothecin and camptothecin, and any derivatives thereof; the lignans etoposide, podophyllotoxin and any derivatives thereof, the Vinca alkaloids vinblastine, vincristine, vindesine and vinorelbine, and any derivatives thereof; calicheamicins and any derivatives thereof; maytansinoids and any derivatives thereof; auristatins and any derivatives thereof; epothilones and any derivatives thereof; bleomycin, dactinomycin, plicamycin, mitomycin C and cis-configured platinum(II) complexes.

In an especially preferred embodiment of the present invention, the LSE oligomer contains at least to different cytostatic agents, or at least one cytostatic agent and at least one MDR modulator.

Each block i may independently contain up to n(i) different effector units. Moreover, the effector units $E_{i,k}$ in two different blocks may be the same or different. This is illustrated for example in FIGS. 2a and 2b. In particular, the oligomer of FIG. 2a contains up to three different effector units $E_{0,0}$, $E_{0,1}$ and $E_{0,2}$, and the oligomer of FIG. 2b contains up to five different effector units $E_{0,0}$, $E_{0,1}$, $E_{0,2}$, $E_{1,1}$ and $E_{2,0}$, However, in a preferred embodiment of the present invention, each block i contains within one block only the same effector units. In total, the linear self-eliminating oligomer of the present invention has to contain at least two effector units $E_{i,k}$.

The LSE oligomer is preferably produced by a synthesis route comprising repeated coupling of the linker units starting from the carrier. In particular, it is especially preferred to synthesize the LSE oligomer by the reaction sequence shown in FIG. 4a (depicted for a monofunctional carrier and m=0). Said reaction sequence comprises the steps of providing a carrier bearing an isocyanate group, coupling a first linker group to said carrier, wherein the first linker group bears a hydroxyl group and one acyl azide group, thermally converting the acyl azide group into an isocyanate group, coupling a second linker group to the first linker group, repeating the previous coupling steps until the oligomer contains n linker groups, and finally coupling the trigger group $T_0$ being bound to a linker group, i.e. $T_0$-$L_{0,0}$-OH, to the terminal linker of the oligomer chain. Coupling of the linker groups is achieved by making use of the Curtius rearrangement wherein an acyl azide is thermally or photochemically converted into an isocyanate. Subsequent reaction of said isocyanate with an alcohol forms a carbamate bond.

A further preferred synthetic route to LSE oligomers is a modification of the above described procedure as depicted in FIG. 4b. In this case, Boc-protected acyl hydrazide containing linkers are employed for the coupling steps. In two consecutive steps, the Boc-protected acyl hydrazide is then converted into the acyl azide. The synthetic route of FIG. 4b is recommended for the case that the respective acyl azide tends to premature decomposition thus leading to inefficient coupling.

It is further preferred to perform single coupling steps of the linker-effector building blocks either according the procedure of FIG. 4a or according to procedure of FIG. 4b, i.e. for each coupling step the optimal procedure is independently selected from the procedures of FIG. 4a and FIG. 4b.

Another preferred synthetic route to LSE oligomers is based on an alternating sequence of Suzuki couplings and hydroboration reactions. This approach is exemplarily shown in FIG. 4c. Said synthetic route has the advantage that aggressive isocyanate chemistry can be avoided. Moreover, most functional groups such as hydroxy groups and amino groups do not deteriorate the synthesis.

Using the above described synthetic methods, it is possible to build up the LSE oligomer of the present invention starting from the carrier which is advantageous from the viewpoint of synthesis. In particular, it is possible to perform carrier-supported synthesis of the LSE oligomer e.g. using a solid phase (similar to the principle of the Merrifield peptide synthesis) or using a soluble polymeric carrier. The use of poly(ethylene glycol) as a soluble polymeric carrier provides the additional advantages of the ease of purification by simple precipitation and the possibility of employing NMR or MALDI-TOF techniques for the characterization of all intermediates.

To the contrary, the linear self-eliminating oligomers known in the prior art are build up using different concepts. The LSE oligomer described in A. Warnecke, F. Kratz, *J. Org. Chem.* 2008, 73, 1546-1552, is produced by the reaction sequence shown in FIG. 1b. In particular, the linear backbone of the oligomer is built up starting from the trigger which is a p-nitrobenzyl group. tert-Butyldimethylsilyl (TBS) monoprotected 2,4-bis(hydroxymethyl)aniline is used as building block for the LSE oligomer backbone. By alternating activation and coupling steps, an oligomer of the TBS-protected monermer is synthesized. For introducing effector molecules, the TBS protective groups have to be removed followed by an activation step and the coupling to of the amino-functionalized effector (tryptamine).

The self-immolative polymers described in Sagi, A.; Weinstain, R.; Karton, N.; Shabat, D. *J. Am. Chem. Soc.* 2008, 130, 5434-5435 are produced by a reaction sequence comprising the polymerization of phenyl carbamate units to obtain a polyurethane and subsequent introduction of the trigger unit.

However, the above concepts are not suitable to build up the LSE oligomer of the) present invention, since it is not possible to obtain an oligomer (i) which has the effector-containing repeating units in between the carrier and the trigger unit, (ii) which may contain several blocks having different trigger units, and (iii) which may contain different effector units within one block of the oligomer. In particular, using the polymerization proposed by Shabat et al., only polydispers compounds are obtained, and a well-defined sequence of different effector units within the polymer is not possible.

According to the present invention, the synthesis of the building block forming the linker group depends on the basic structure of the linker group. For example, to obtain a linker group $L_{i,k}$ having above structure (II) with $R_2$ being hydrogen and $R_1$ being

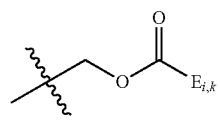

the following building block (VII) may be used. Said compound (VII) can be synthesized starting from the more general building block (VI):

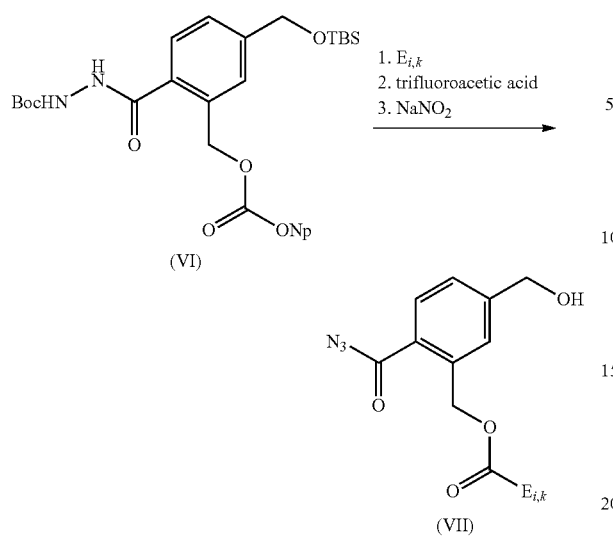

(VI)

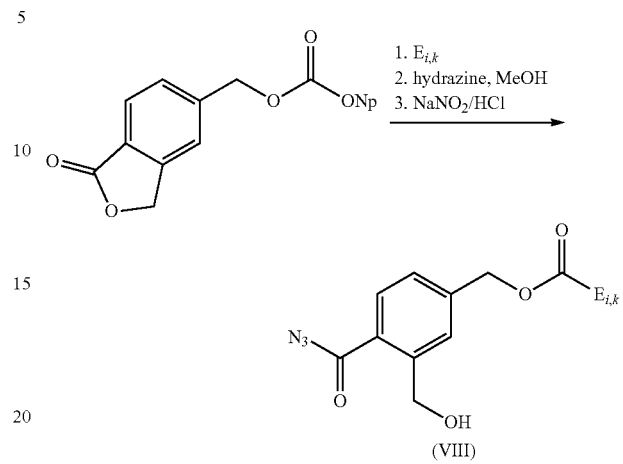

in a preferred embodiment, above building block (VIII) is obtained by a different synthetic route, namely by the following reaction:

(VII)

(VIII)

wherein "TBS" means tert-butyldimethylsilyl, "Np" means 4-nitrophenyl, and "Boc" means tert-butyloxycarbonyl. In particular, starting from compound (VI), an amino-functionalized effector unit $E_{i,k}$ is introduced, the protective groups are removed by trifluoroacetic acid, and the azide group is introduced e.g. by sodium nitrite/hydrochloric acid.

In the same manner, the following building blocks (VIM) to (X) can be used for the synthesis of LSE oligomers comprising above linker units (III) and (IV):

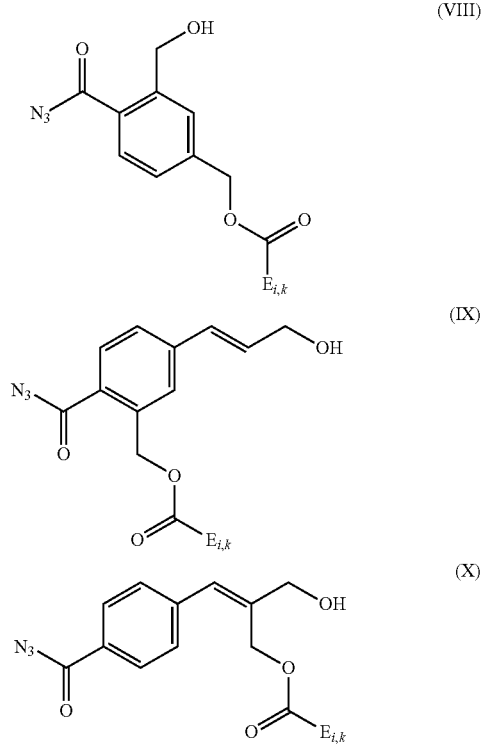

(VIII)

(IX)

(X)

The synthesis of the above examples for possible building blocks is analogous to the synthesis of building block (VI) and is within the skills of a person skilled in the art. However, Another aspect of the present invention relates to a pharmaceutical composition, comprising the LSE oligomer as defined above, and optionally a pharmaceutically acceptable carrier and/or a pharmaceutically acceptable adjuvent and/or a diluent.

The pharmaceutical composition may for example contain solvents and diluents such as sodium chloride solution or a solution containing any pharmaceutically acceptable buffer. Moreover, the pharmaceutical composition of the present invention may be in any form suitable for administration to a patient, for example in an injectable form, as a tablette or a capsule, or as a composition for inhalation.

According to a specific embodiment, the above-defined pharmaceutical composition is for treatment of a disease selected from the group consisting of cancer, autoimmune diseases, acute or chronic inflammatory diseases, and diseases caused by viruses and/or microorganisms.

Another aspect of the present invention relates to the use of the LSE oligomer as defined above in the manufacturing of a pharmaceutical composition for treating or diagnosing a patient suffering from a disease selected from the group consisting of cancer, autoimmune diseases, acute or chronic inflammatory diseases, and diseases caused by viruses and/or microorganisms.

According to a further specific embodiment, the above-defined pharmaceutical composition is for the treatment of cancer in which one type of receptor or antigen is overexpressed compared to healthy tissue.

According to another embodiment of the present invention, the LSE oligomer as defined above may be comprised in a kit, which may further contain one or more adjuvants, such as a buffer or a pharmaceutically acceptable carrier.

The Figures Show:

According to the present invention, a linear self-eliminating oligomer is provided which is suitable to release effector molecules upon activation, which can be loaded with different effector molecules in a straightforward synthetic manner, and which does not lead to a complete deattachment of the linker-effector units from the carrier upon activation of the trigger in view of the arrangement of the linker-effector units in between the trigger and the carrier.

The present invention is illustrated in the following example without any limitation thereto.

EXAMPLES

Synthesis of the Activated Linker Precursor

Figure 1A:
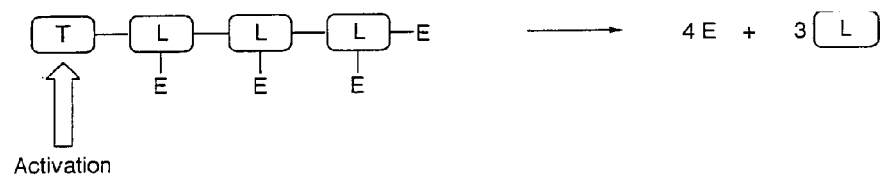
FIG. 1 shows linear self-eliminating oligomers according to the prior art.
Figure 1B:
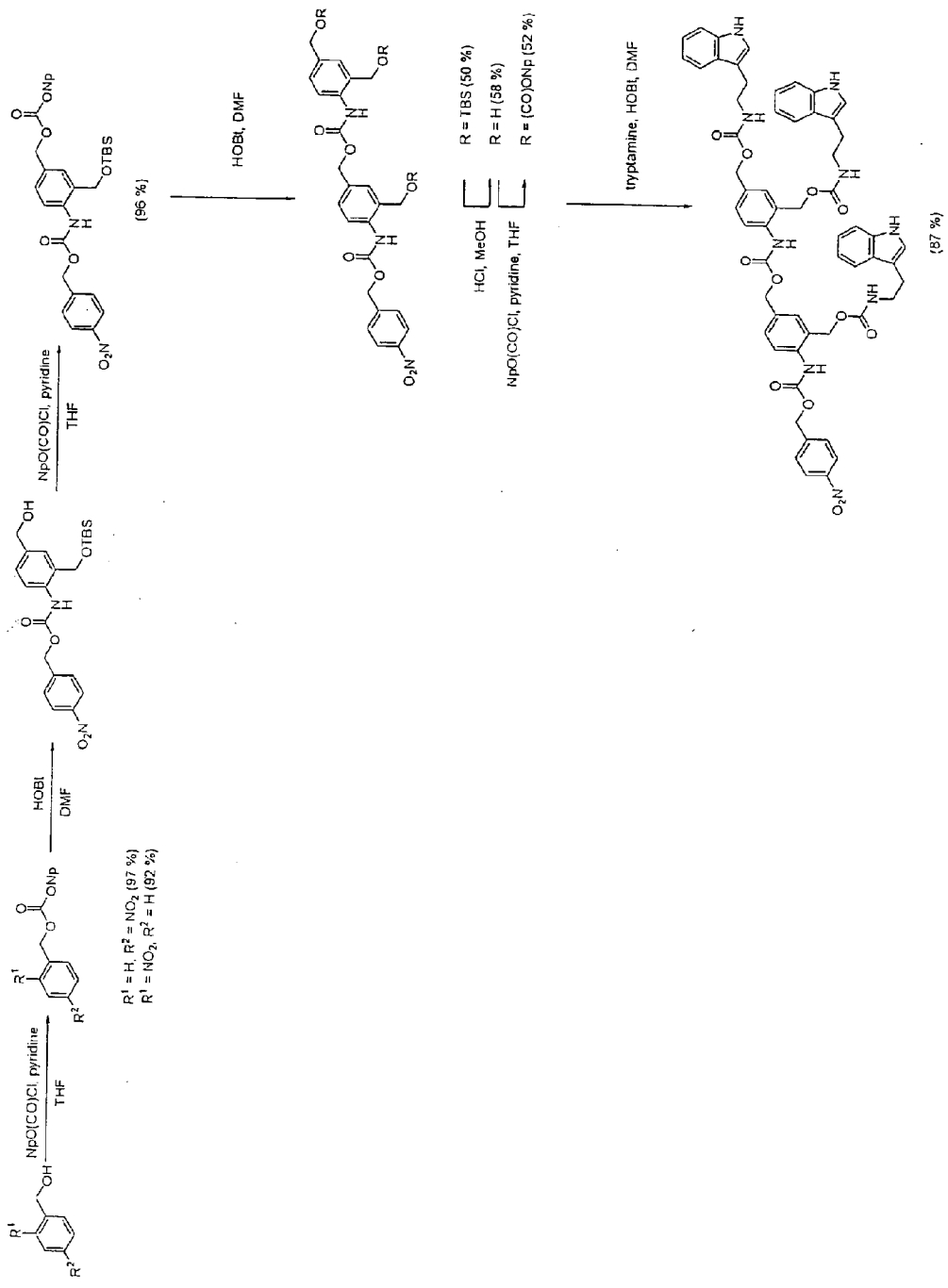
Figure 2A:
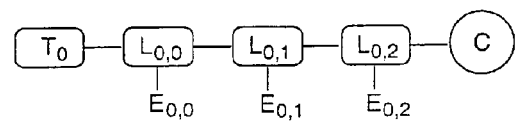
FIG. 2 shows the linear self-eliminating oligomers according to the present invention.
Figure 2B:
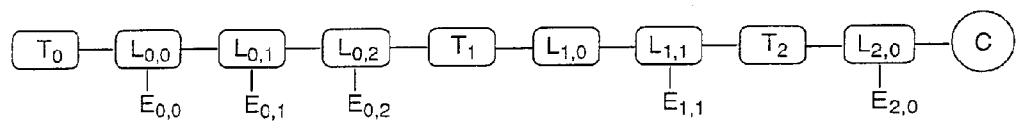
Figure 2C:
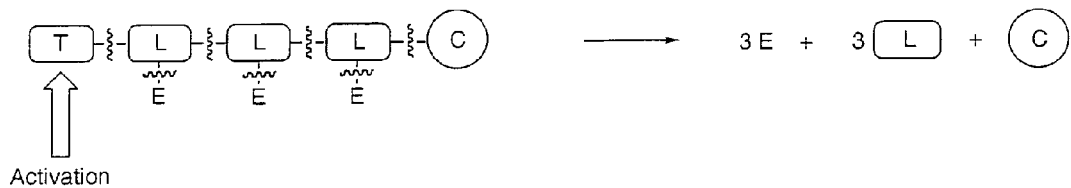
Figure 2D:
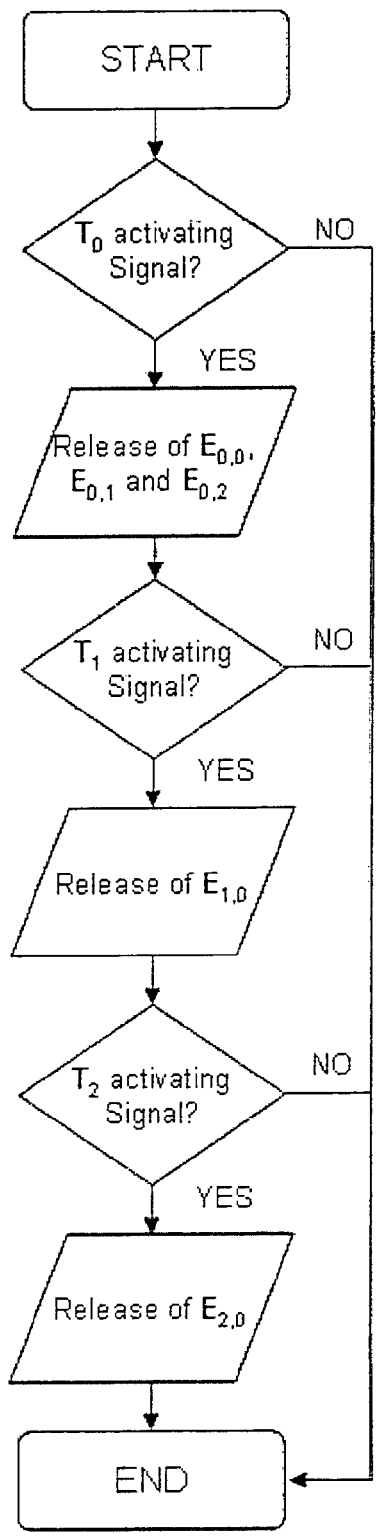
Figure 3:
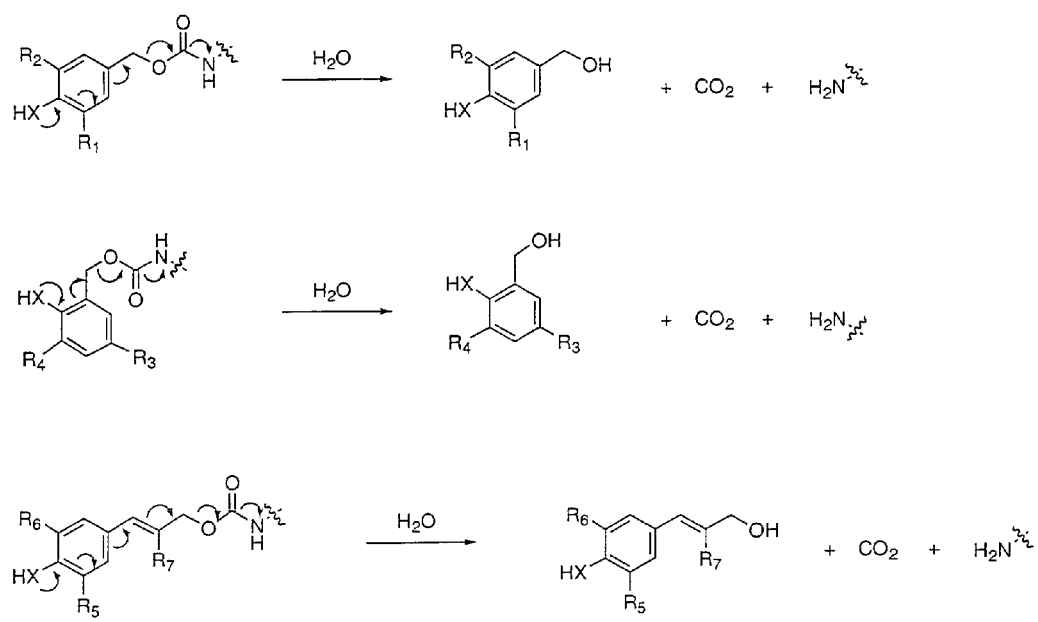
FIG. 3 shows the disassembling mechanisms of the different linker units.
Figure 4A:
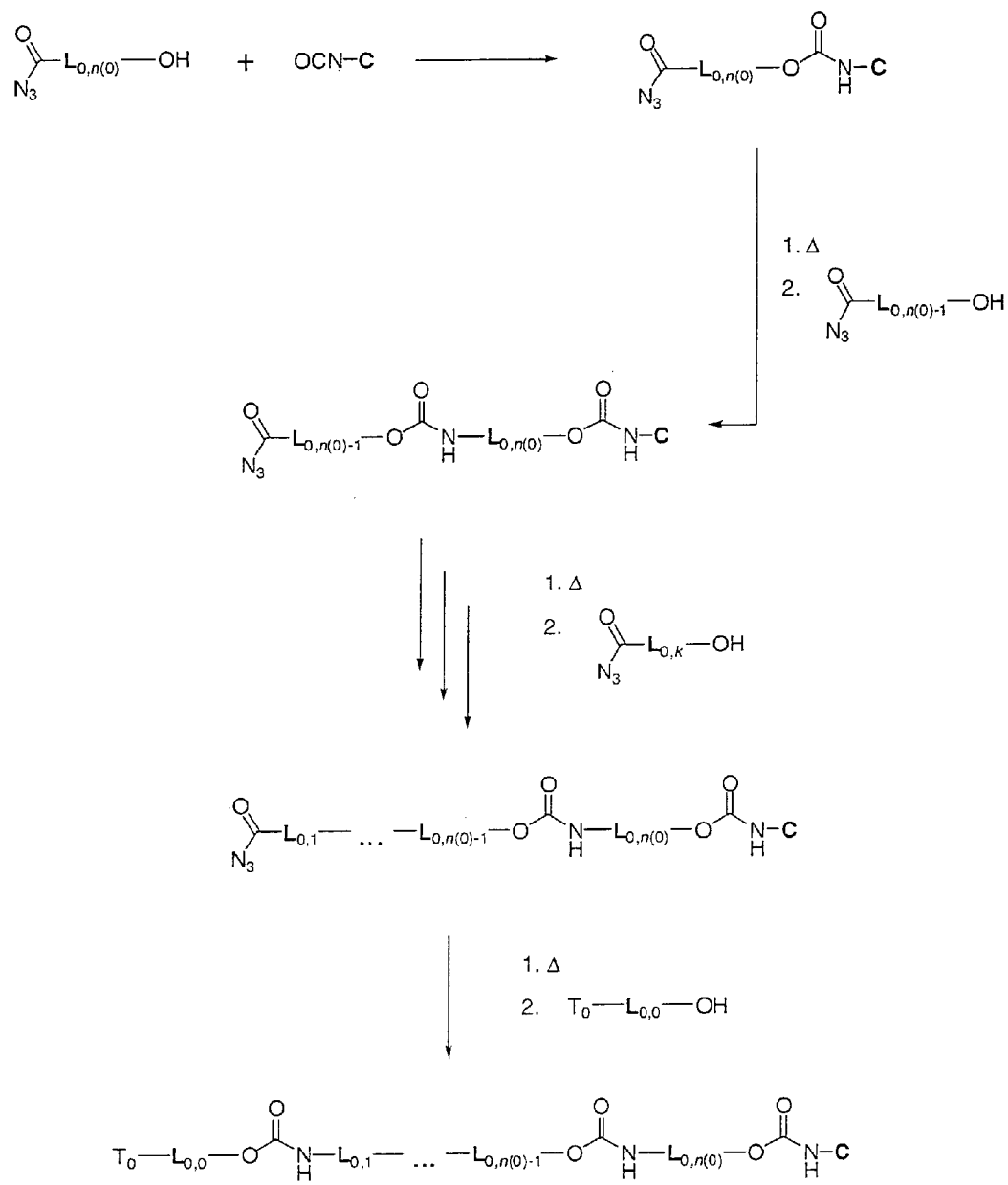
FIG. 4 shows the synthesis of the LSE oligomer of the present invention.
Figure 4B:
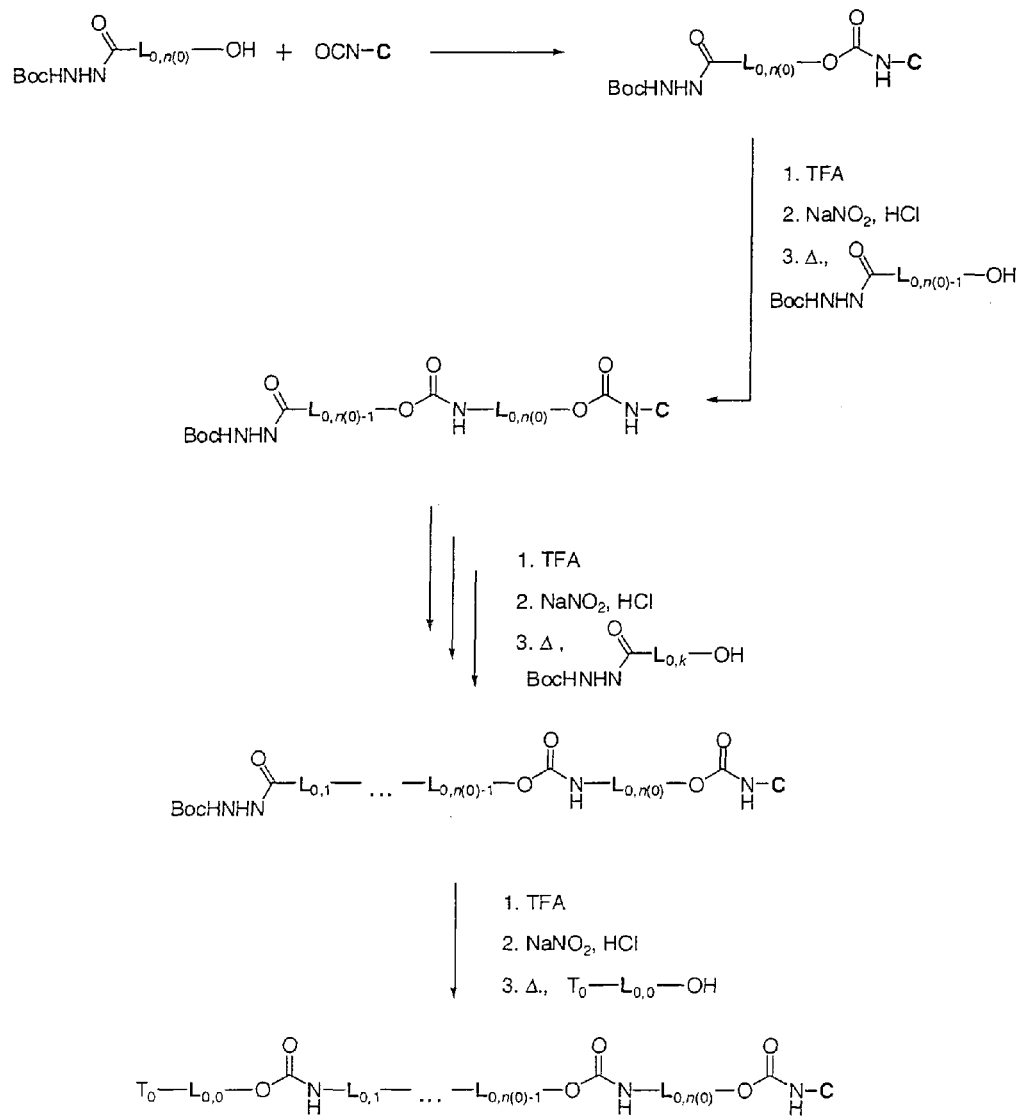
Figure 4C:
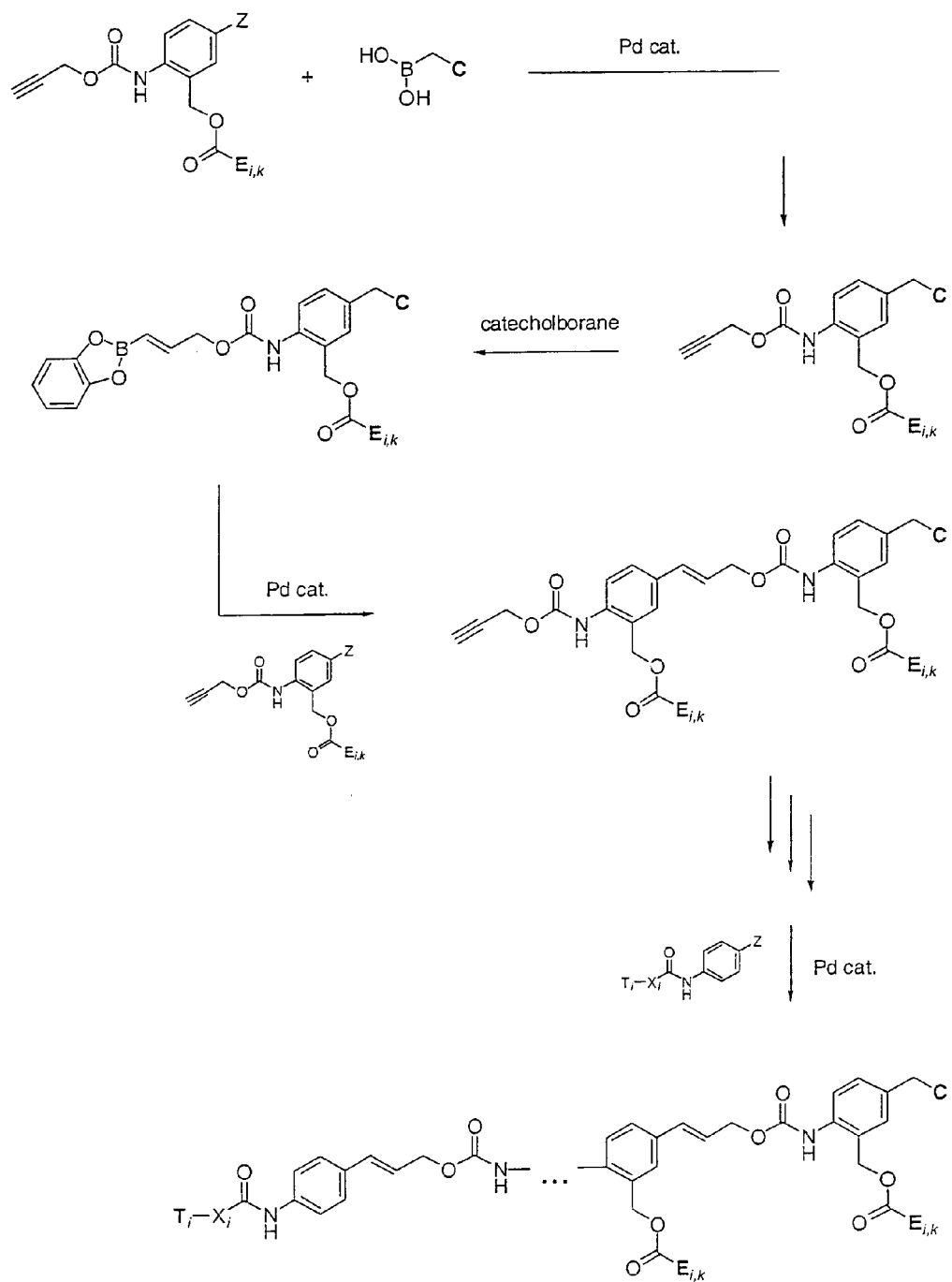
Figure 5A:
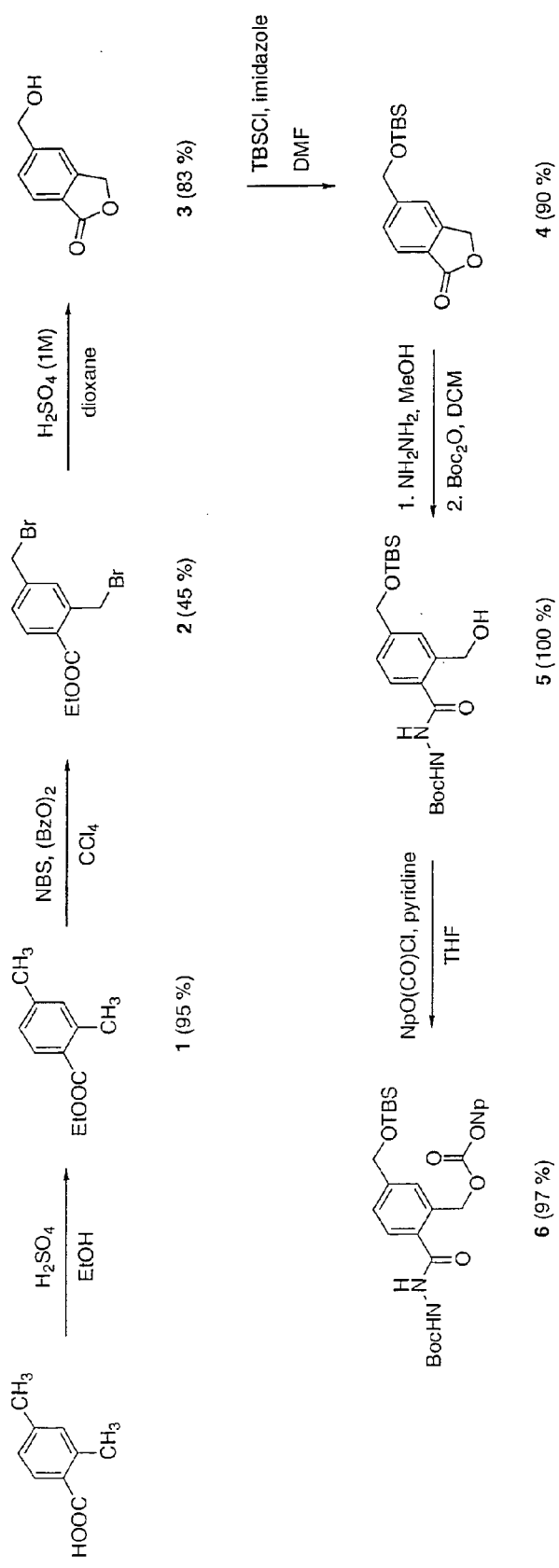
FIG. 5 shows the synthesis of a LSE oligomer according to an Example.

The synthesis of the activated linker precursor has been performed as shown in FIG. 5a.

Ethyl 2,4-Dimethylbenzoate (1). To a solution of commercially available 2,4-dimethylbenzoic acid (67.8 g, 451 mmol) in 1000 mL of ethanol was added 10 mL of sulfuric acid. The mixture was refluxed over night, cooled down and was neutralized by adding calcium hydroxide in small portions (~30 g). The suspension was filtered over celite and concentrated in vacuo. The crude product was purified by vacuum distillation yielding 76.4 g (95%) of 1 as a colorless oil: $^1$H-NMR (400 MHz, CDCl$_3$): δ 1.38 (t, J=7.3 Hz, 3H), 2.34 (s, 3H), 2.57 (s, 3H), 4.33 (q, J=7.2 Hz, 2H), 7.01-7.06 (m, 2H), 7.82 (d, J=8.5 Hz, 1H); $^{13}$C-NMR (100 MHz, CDCl$_3$): δ 14.3, 21.3, 21.7, 60.4, 126.3, 126.9, 130.7, 132.4, 140.1, 142.3, 167.6; MS (ESI) m/z=133.0 (100), 132.0 (57), 178.1 (M$^+$, 51).

Ethyl 2,4-Bis(bromomethyl)benzoate (2). To a suspension of 1 (48.4 g, 272 mmol) and NBS (97.0 g, 544 mmol) in CCl$_4$ (600 mL) was added a 20-mg portion of (BzO)$_2$ and the reaction mixture was heated under reflux for 2.5 h. The solids were removed by filtration over celite, washed with DCM, and the filtrate was concentrated in vacuo. The residue was crystallized from EtOAc/hexane affording 41.5 g (45%) of pure 2 as a colorless solid: $^1$H-NMR (400 MHz, CDCl$_3$): δ 1.42 (t, J=7.2 Hz, 3H), 4.40 (q, J=7.1 Hz, 2H), 4.46 (s, 2H), 4.93 (s, 2H), 7.39 (dd, J$_1$=1.9 Hz, J$_2$=8.1 Hz, 1H), 7.47 (d, J=1.8 Hz, 1H), 7.94 (d, J=8.1 Hz, 1H); $^{13}$C-NMR (100 MHz, CDCl$_3$): δ 14.2, 29.5, 31.0, 31.6, 61.4, 128.9, 129.3, 131.8, 132.0, 139.7, 142.1, 166.1; MS (CI$^+$ (NH$_3$)) m/z=353.9 (M+NH$_4^+$, 100), 351.9 (M+NH$_4^+$, 50), 355.9 (M+NH$_4^+$, 48).

5-Hydroxymethylphthalide (3). A suspension of 2 (22.1 g, 65.7 mmol) in 700 mL of a 1:1 mixture of dioxane/sulfuric acid (1M) was heated under reflux for 20 h. After cooling to room temperature, the mixture was poured into 200 mL of DCM. The phases were separated and the aqueous phase was extracted with DCM (5×200 mL). The combined organic layers were washed with saturated NaHCO$_3$ (3×200 mL) and brine (1×200 mL) and were dried over MgSO$_4$. The solvent was removed in vacuo to yield 8.70 g (83%) of pure 3 as a colorless solid: $^1$H-NMR (400 MHz, DMSO-d$_6$): δ 4.65 (s, 2H), 5.39 (s, 2H), 5.47 (br s, 1H), 7.51 (d, J=7.8 Hz, 1H), 7.60 (s, 1H), 7.78 (d, J=7.7 Hz, 1H); $^{13}$C-NMR (100 MHz, DMSO-d$_6$): δ 62.4, 69.7, 120.0, 123.3, 124.5, 126.9, 147.5, 149.7, 170.5; MS (CI$^+$ (NH$_3$)) m/z=165.0 (M+H$^+$, 100), 182.0 (M+NH$_4^+$, 49).

5-((tert-Butyldimethylsilyloxy)methylphthalide (4). A solution of 3 (10.0 g, 60.9 mmol) in anhydrous DMF (60 mL) was added dropwise within 15 min to a stirred solution of tert-butyldimethylchlorosilane (13.8 g, 91.4 mmol) and imidazole (6.22 g, 91.4 mmol) in anhydrous DMF (50 mL). After stirring at room temperature for 16 h, the reaction mixture was poured into water (200 mL) and extracted with DCM (3×100 mL). The combined organic layers were washed with water (2×100 mL) and dried over MgSO$_4$. After removing the volatiles in vacuo, the residue was recrystallized from n-hexane (100 mL) affording 15.3 g (90%) of pure 4 as colorless crystals: $^1$H-NMR (400 MHz, DMSO-d$_6$): δ 0.11 (s, 6H), 0.92 (s, 9H), 4.87 (s, 2H), 5.41 (s, 2H), 7.50 (d, J=8.1 Hz, 1H), 7.60 (s, 1H), 7.81 (d, J=7.8 Hz, 1H); $^{13}$C-NMR (100 MHz, DMSO-d$_6$): δ -5.4, 18.0, 25.8, 63.9, 69.8, 119.7, 123.7, 124.7, 126.5, 147.7, 148.3, 170.5; MS (CI$^+$ (NH$_3$)) m/z=296.2 (M+NH$_4^+$, 100).

tert-Butyl 2-(4-((tert-Butyldimethylsilyloxy)methyl)-2-(hydroxymethyl)benzoyl)hydrazinecarboxylate (5). To a solution of 4 (15.0 g, 53.9 mmol) in 150 mL of methanol was added hydrazine hydrate (7.8 mL, 161 mmol) dropwise within 10 min. After stirring for 16 h at ambient temperature, the volatiles were removed in vacuo. Dissolving the crude material in a minimum amount of ethyl acetate followed by precipitation with hexane yielded the acyl hydrazide which in turn was subjected to Boc protection. For this purpose, the acyl hydrazide dissolved in 200 mL of DCM was treated with di-tert-butyl dicarbonate (29.4 g, 135 mmol). After stirring at room temperature for 16 h, the volatiles were removed in vacuo and the residue was recrystallized from ethyl acetate/hexane affording 22.1 g (100%) of 5 as colorless solid: $^1$H-NMR (400 MHz, DMSO-d$_6$): δ 0.09 (s, 6H), 0.92 (s, 9H), 1.43 (s, 9H), 4.64 (s, 2H), 4.75 (s, 2H), 5.21 (br s, 1H), 7.24 (d, J=7.8 Hz, 1H), 7.32-7.43 (m, 1H), 7.55 (s, 1H), 8.91 (s, 1H), 9.91 (br s, 1H); $^{13}$C-NMR (100 MHz, DMSO-d$_6$): δ -5.3, 18.1, 25.8, 28.1, 60.6, 64.1, 79.2, 123.8, 124.6, 127.3, 131.1, 141.1, 143.3, 155.4, 168.1; MS) (TOF) m/z=433.2 (M+Na$^+$, 100).

tert-Butyl 2-(4-((tert-Butyldimethylsilyloxy)methyl)-2-(((4-nitrophenoxy)carbonyloxy)methyl)benzoyl)hydrazinecarboxylate (6). To a solution of 4-nitrophenyl chloroformate (1.10 g, 5.48 mmol) in 40 mL of anhydrous THF was added pyridine (390 µL, 5.48 mmol) at 0° C. After stirring for 15 min, a solution of 5 (1.50 g, 3.65 mmol) in 15 mL of anhydrous THF was added dropwise within 10 min, and the mixture was allowed to warm up. Stirring was continued at room temperature for 16 h after which 50 mL DCM was added. The mixture was washed with 1M HCl (3×60 mL) and brine (1×50 mL), and the aqueous layers were re-extracted with DCM. The combined organic phases were dried over MgSO$_4$ and the volatiles were removed in vacuo. Flash chromatography of the crude product (1:2 EtOAc-hexane) afforded 6 (97%) as a colorless solid: $^1$H-NMR (400 MHz, CDCl$_3$): δ 0.11 (s, 6H), 0.94 (s, 9H), 1.49 (s, 9H), 4.79 (s, 2H), 5.58 (s, 2H), 6.71 (br s, 1H), 7.37-7.42 (m, 3H), 7.54 (s, 1H), 7.61 (d, J=8.1 Hz, 1H), 7.96 (br s, 1H), 8.23-8.29 (m, 2H); $^{13}$C-NMR (100 MHz, CDCl$_3$): δ -5.1, 18.5, 26.0, 28.3, 64.3, 68.5, 82.3, 121.9, 125.4, 126.5, 127.4, 128.3, 131.4, 133.6, 145.5, 145.7, 152.5, 155.5, 155.6, 168.0; MS (TOF) m/z=598.2 (M+Na$^+$, 100).

Synthesis of Linker-Effector Building Blocks

Figure 5B:
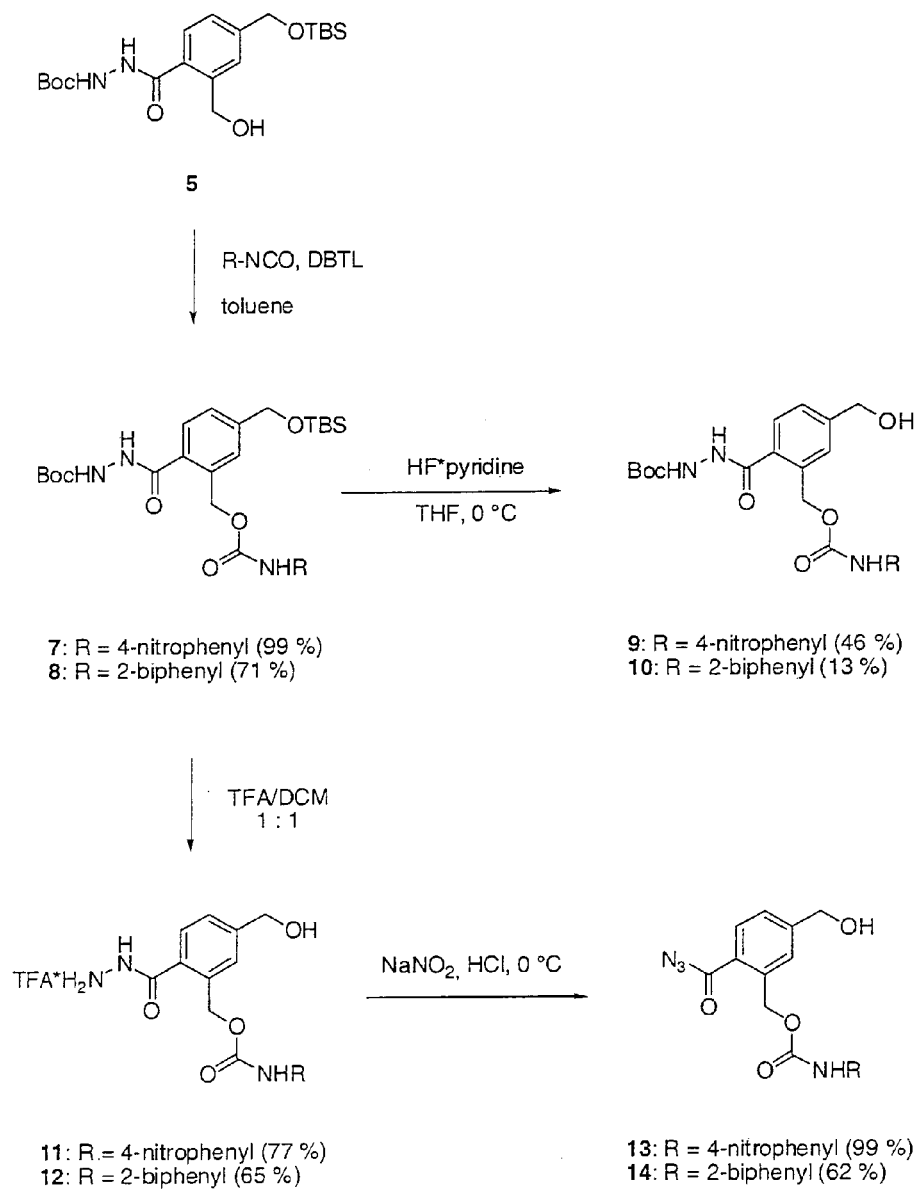

The synthesis of linker-effector building blocks has been performed as shown in FIG. 5b.

Using p-nitroaniline and 2-aminobiphenyl as model effector molecules, the respective isocyanates were reacted with 6 to afford the Boc- and TBS-protected intermediates 7 and 8.

Selective removal of the TBS protective group using HF*pyridine afforded the building blocks 9 and 10 which were further used for the synthesis of the model LSE oligomer.

Alternative building blocks were obtained from 7 and 8 by first removal of both the Boc and TBS protective groups using trifluoroacetic acid followed by a reaction with sodium nitrite and hydrochloric acid. The building blocks 13 and 14 having both an acyl azide group and a free hydroxy group were shown to be sufficiently stable when stored at −80° C.

Synthesis of a Simple LSE Oligomer that is Cleaved by α-Chymotrypsin

Figure 5C:
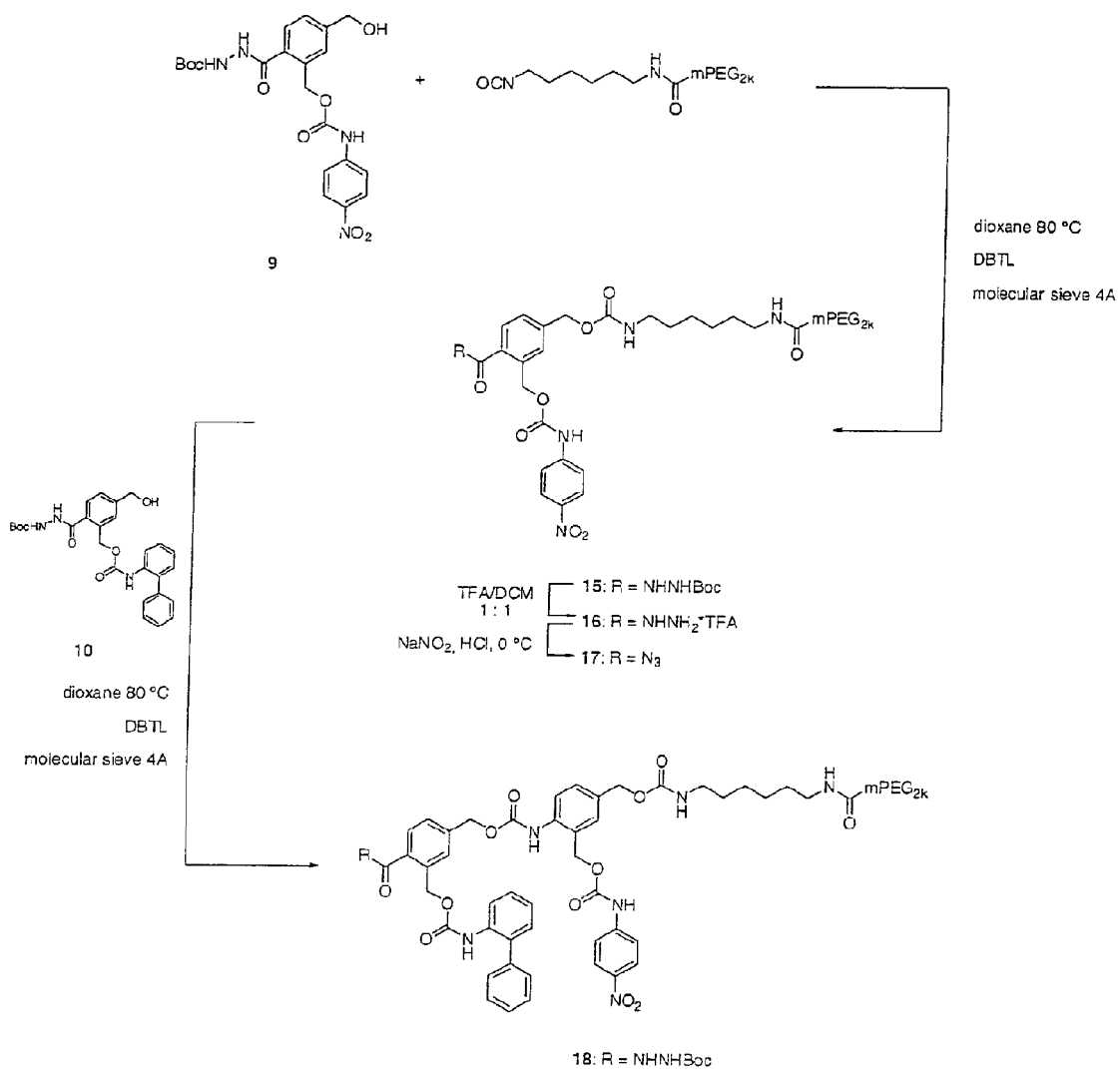

The synthesis of a simple LSE oligomer that is cleaved by α-chymotrypsin has been performed as shown in FIG. 5c.

In a first step, monomer 9 was conjugated with isocyanate-functionalized mPEG using DBTL (dibutyltin dilaurate) as a catalyst. After removal of the Boc protective group using TFA, the acyl hydrazide (16) was converted to the acyl azide (17) employing sodium nitrite and hydrochloric acid.

Acyl azide 17 was heated to undergo a Curtius rearrangement to the respective isocyanate so that the next building block (10) could be coupled using DBTL (dibutyltin dilaurate) as a catalyst. After removal of the Boc protective group using TFA, the acyl hydrazide (19) was converted to the acyl azide (20) employing sodium nitrite and hydrochloric acid.

Acyl azide 20 was heated to undergo a Curtius rearrangement to the respective isocyanate so that the trigger group Ac-Phe-PABA ((S)-2-acetamido-N-(4-(hydroxymethyl)phenyl)-3-phenylpropanamide) could be coupled using DBTL (dibutyltin dilaurate) as a catalyst.

The final product (21) and all intermediates were conveniently purified by precipitation from diethyl ether (typically 100 mL diethyl ether per 100 mg of conjugate).

LSE oligomer 21 proved to have an excellent solubility in aqueous media.

Activation of the LSE Oligomer 21 by α-Chymotrypsin

A solution of 6.4 mg (2 μmol) of 21 in 2 mL phosphate buffer (pH 7.8) was divided into two portions. To one of these samples was added 1 mg of α-chymotrypsin, and the samples were stored in a heating block at 37° C. for 24 h. Subsequently, the samples were mixed with 500 μL of dichloromethane and the organic layers were analyzed by TLC (hexane-ethyl acetate 3:1). The sample that was incubated with the enzyme showed two spots referring to the two effector molecules p-nitroaniline and 2-aminobiphenyl, respectively, whereas the control sample did not show any release of the effectors.

What is claimed is:

1. A linear self-eliminating oligomer having the following formula (I):

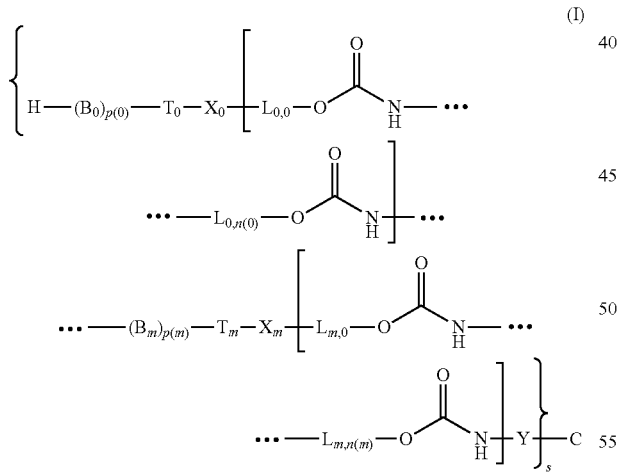

wherein
$T_{i\ (i=0\ to\ m)}$ is a trigger group which can be cleaved hydrolytically, enzymatically, pH-dependently, thermally, photochemically, oxidatively or reductively;
$X_{i\ (i=0\ to\ m)}$ is NH, O or S;
C is a carrier selected from the group consisting of serum proteins, antibodies or antibody fragments, synthetic polymers, dendrimers, peptides, growth factors, receptor-binding ligands, polysaccharides, microparticles and nanoparticles;
Y is a single bond or a spacer group;

m is 0 to 5;
s is 1 to 100;
$n(i)_{(i=0\ to\ m)}$ is independently 1 to 30;
  with the proviso that n(0) is at least 2 when m=0;
$p(i)_{(i=0\ to\ m)}$ is independently 0 or 1;
  with the proviso that p(0) is 0;
$L_{i,k\ (i=0\ to\ m\ and\ k=0\ to\ n(i))}$ is a linker unit independently selected from one of the following structures (II), (III), (IV) or (V):

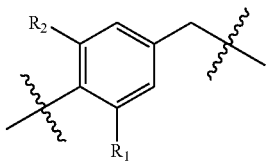

(II)

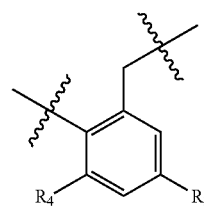

(III)

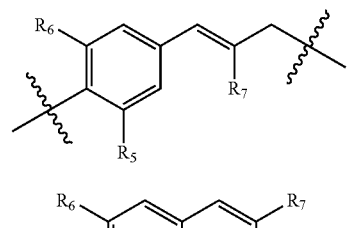

(IV)

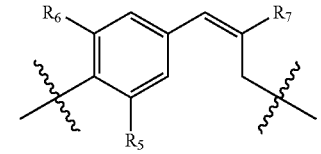

(V)

$B_{i\ (i=0\ to\ m)}$ is a blocking unit having the following structure:

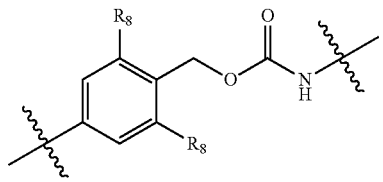

$R_1$ is selected from H or one of the following residues:

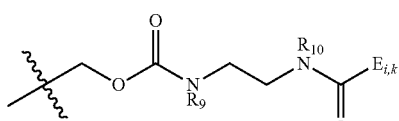

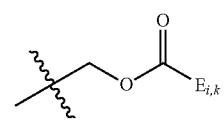

$R_2$ is selected from H, methyl, $CH_3O$, halogen, acetyl, alkoxycarbonyl, $NO_2$ or one of the following residues:

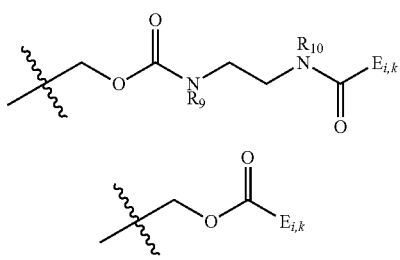

$R_3$ is selected from H or one of the following residues:

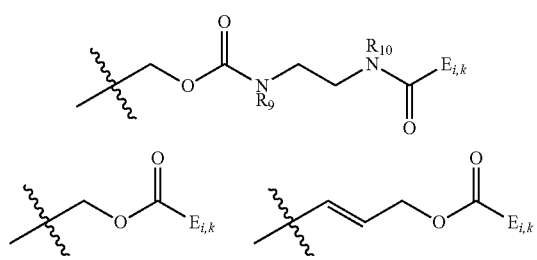

$R_4$ is selected from H, methyl, $CH_3O$, halogen, acetyl, alkoxycarbonyl, $NO_2$ or one of the following residues:

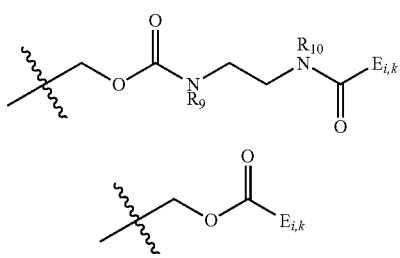

$R_5$ is selected from H or one of the following residues:

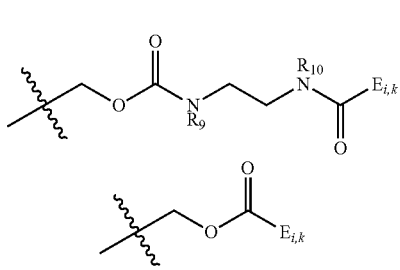

$R_6$ is selected from H, methyl, $CH_3O$, halogen, acetyl, alkoxycarbonyl, $NO_2$ or one of the following residues:

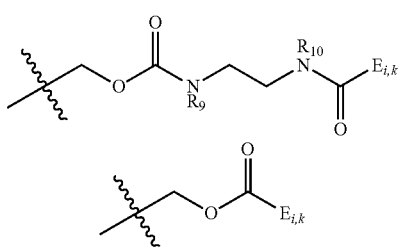

$R_7$ is selected from H or one of the following residues:

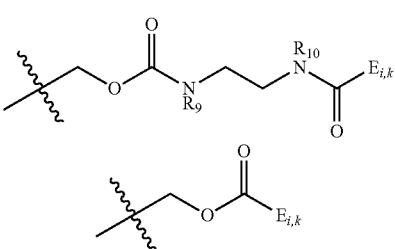

$R_8$ is independently selected from a linear or branched $C_{1-8}$ alkyl group, a phenyl group, a naphthyl group, a biphenyl group or a vinyl benzene group;

$R_9$ is independently selected from hydrogen or a linear or branched $C_{1-8}$ alkyl group;

$R_{10}$ is independently selected from hydrogen or a linear or branched $C_{1-8}$ alkyl group;

$E_{i,k\ (i=0\ to\ m\ and\ k=0\ to\ n(i))}$ is an effector group independently containing a dye, a diagnostic agent or a pharmaceutically active compound, wherein the dye, diagnostic agent or pharmaceutically active compound is bound to the linker unit $L_{i,k}$ via an amino, hydroxy or mercapto group;

with the proviso that the linear self-eliminating oligomer contains in total at least two effector units.

2. The linear self-eliminating oligomer according to claim 1, wherein at least all linker units $L_{i,k}$ with k>0 have the following structure (II):

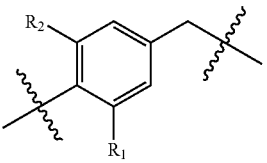

3. The linear self-eliminating oligomer according to claim 2, wherein $R_1$ has the following structure:

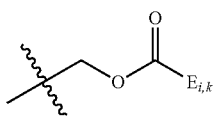

4. The linear self-eliminating oligomer according to claim 2, wherein $R_1$ and $R_2$ are hydrogen in the linker unit $L_{i,0}$ being adjacent to the structural unit $T_i$-$X_i$.

5. The linear self-eliminating oligomer according to claim 2, wherein $R_2$ is hydrogen or the following residue:

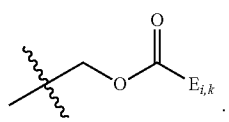

6. The linear self-eliminating oligomer according to claim 1, wherein m is 1 to 5.

7. The linear self-eliminating oligomer according to claim 6, wherein at least one of p(i) is 1, and the residue $R_8$ in the blocking unit $B_i$ is tert-butyl.

8. The linear self-eliminating oligomer according to claim 1, wherein m is 0.

9. The linear self-eliminating oligomer according to claim 1, wherein the spacer unit Y has the following structure:

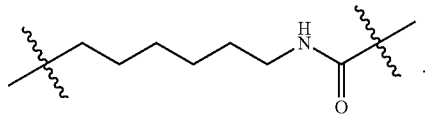 [SMILES: *CCCCCCNC(*)=O]

10. The linear self-eliminating oligomer according to claim 1, wherein the effector unit $E_{i,k}$ is independently selected from the group consisting of a cytostatic agent, a cytokine, an immunosuppressant, an antirheumatic, an antiphlogistic, an antibiotic, an analgetic, a virostatic, an antimycotic agent, a transcription factor inhibitor, a cell cycle modulator, a MDR modulator, a vascular disrupting agent, a proteasome or protease inhibitor, an apoptosis modulator, an enzyme inhibitor, an angiogenesis inhibitor, a hormone or hormone derivative, a radioactive substance, a light emitting substance, and a light absorbing substance.

11. The linear self-eliminating oligomer according to claim 10, wherein the effector unit $E_{i,k}$ is a cytostatic agent selected from the group consisting of N-nitrosoureas, the anthracyclines doxorubicin, daunorubicin, epirubicin, idarubicin, mitoxantrone and ametantrone, and any derivatives thereof; the alkylating agents chlorambucil, bendamustine, melphalan, and oxazaphosphorines, and any derivatives thereof; the antimetabolites 5-fluorouracil, 2'-deoxy-5-fluorouridine, cytarabine, cladribine, fludarabine, pentostatine, gemcitabine, 6-thioguanine, 6-mercaptopurine and any derivatives thereof; the folic acid antagonists methotrexate, raltitrexed, pemetrexed and plevitrexed, the taxanes paclitaxel and docetaxel, and any derivatives thereof; the camptothecins topotecan, irinotecan (CPT-11), SN-38, 10-hydroxycamptothecin, GG211, lurtotecan, 9-aminocamptothecin and camptothecin, and any derivatives thereof; the lignans etoposide, podophyllotoxin and any derivatives thereof; the Vinca alkaloids vinblastine, vincristine, vindesine and vinorelbine, and any derivatives thereof; calicheamicins and any derivatives thereof; maytansinoids and any derivatives thereof; auristatins and any derivatives thereof; epothilones and any derivatives thereof; bleomycin, dactinomycin, plicamycin, mitomycin C and cis-configured platinum(II) complexes.

12. The linear self-eliminating oligomer according to claim 1, wherein the cleavable trigger group $T_i$ is independently selected from the group consisting of enzymatically cleavable peptide sequences, said enzymatically cleavable peptide sequences comprising -Arg-, -Arg-Arg-, -Phe-Arg-, -Phe-Cit-, -Ile-Pro-Lys-, -Lys-Lys-, -Arg-Lys-, -Ala-Leu-Ala-Leu-, -Phe-Lys-, -Phe-Lys-Ala-, -Val-Cit-, -Val-Arg-, -Ala-Phe-Lys-, -D-Ala-Phe-Lys-, -Ser-Ser-Tyr-Tyr-Ser-Arg-, -Phe-Pro-Lys-Phe-Phe-Ser-Arg-Gln-, -Lys-Pro-Ile-Glu-Phe-Nph-Arg-Leu-, -Gly-Pro-Leu-Gly-Ile-Ala-Gly-Gln-, -Gly-Pro-Leu-Gly-Ile-Ala-Gly-Gln-, -Gly-Pro-Gln-Gly-Ile-Trp-Gly-Gln-, -Gly-Phe-Leu-Gly-, and reductively cleavable groups including

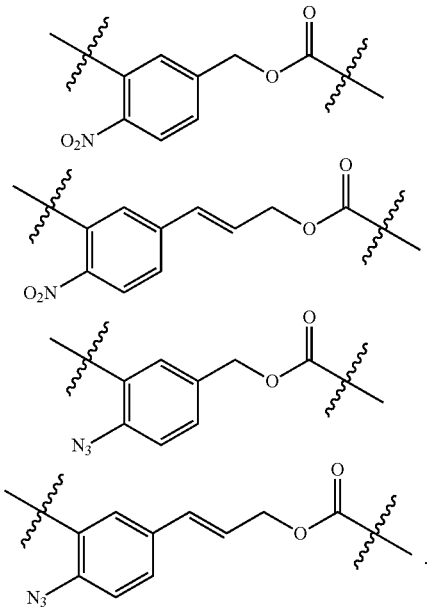

13. The linear self-eliminating oligomer according to claim 1, wherein the carrier C is a synthetic polymer selected from the group consisting of poly(ethylene glycol) (PEG), monomethoxy PEG (mPEG), polyglycerol (PG), poly(ethylene imine) (PEI) and N-(2-hydroxypropyl)methacrylamide (HPMA) copolymers.

14. The linear self-eliminating oligomer according to claim 1, wherein each n(i) is independently 2 to 5.

15. A pharmaceutical composition comprising the linear self-eliminating oligomer according to claim 1, and optionally a pharmaceutically acceptable carrier and/or a pharmaceutically acceptable adjuvant and/or a diluent.

* * * * *